(12) United States Patent
Fujita et al.

(10) Patent No.: US 8,520,974 B2
(45) Date of Patent: Aug. 27, 2013

(54) IMAGE PROCESSING METHOD, AN APPARATUS THEREFOR AND A TOMOGRAPHIC APPARATUS FOR REMOVING ARTIFACTS FROM A SECTIONAL IMAGE

(75) Inventors: Akinori Fujita, Kyoto (JP); Yen-Wei Chen, Kusatsu (JP); Guifang Duan, Kusatsu (JP)

(73) Assignees: Shimadzu Corporation, Kyoto (JP); The Ritsumeikan Trust, Kyoto (JP)

( * ) Notice: Subject to any disclaimer, the term of this patent is extended or adjusted under 35 U.S.C. 154(b) by 260 days.

(21) Appl. No.: 12/812,223

(22) PCT Filed: Jan. 11, 2008

(86) PCT No.: PCT/JP2008/050266
§ 371 (c)(1),
(2), (4) Date: Jul. 8, 2010

(87) PCT Pub. No.: WO2009/087777
PCT Pub. Date: Jul. 16, 2009

(65) Prior Publication Data
US 2010/0284599 A1    Nov. 11, 2010

(51) Int. Cl.
*G06K 9/40*    (2006.01)
*G06K 9/00*    (2006.01)

(52) U.S. Cl.
USPC ............................ 382/275; 382/128; 382/131

(58) Field of Classification Search
USPC ................ 382/128, 129, 130, 131, 132, 133, 382/134, 265, 275; 378/4, 21, 23, 24, 25, 378/378/26, 27, 28, 46, 90, 92, 98.4, 98.6, 378/98.9, 101, 40, 901, 240.19
See application file for complete search history.

(56) References Cited

U.S. PATENT DOCUMENTS

| 5,400,377 | A  |   | 3/1995  | Hu et al. |
| 5,561,695 | A  | * | 10/1996 | Hu ..................................... 378/8 |
| 6,044,125 | A  | * | 3/2000  | Flohr et al. ......................... 378/4 |
| 6,801,646 | B1 | * | 10/2004 | Pena et al. ..................... 382/131 |

(Continued)

FOREIGN PATENT DOCUMENTS

| JP | 7-143979 A | 6/1995 |
| JP | 9-187452 A | 7/1997 |

(Continued)

OTHER PUBLICATIONS

"Independent Component Analysis of Four-Phase Abdominal CT images" (X. Hu et al., Proc. Medical Image Computing and Computer-Assisted Intervention (MICCAI 2004), Lecture Notes in Computer Science, vol. 3217, pp. 916-924, 2004.*

(Continued)

*Primary Examiner* — Andrae S Allison
(74) *Attorney, Agent, or Firm* — Cheng Law Group, PLLC

(57) ABSTRACT

A tomographic apparatus of this invention includes a dividing unit for dividing a sectional image into a pixel group including artifacts and a pixel group not including artifacts by carrying out an independent component analysis (ICA) of the artifacts, and a pixel group processing unit for applying a smoothing filter as a predetermined process relating to correction only with respect to the above pixel group including the artifacts, whereby a correction process is carried out to remove the artifacts. Thus, the artifacts can be removed stably.

9 Claims, 10 Drawing Sheets

(56) References Cited

U.S. PATENT DOCUMENTS

| | | | |
|---|---|---|---|
| 7,406,211 B2* | 7/2008 | Pena et al. | 382/275 |
| 7,519,207 B2* | 4/2009 | Luo et al. | 382/128 |
| 7,680,240 B2* | 3/2010 | Manjeshwar et al. | 378/4 |
| 2007/0058883 A1* | 3/2007 | Xing | 382/275 |
| 2010/0239145 A1* | 9/2010 | Fujita | 382/131 |
| 2011/0123095 A1* | 5/2011 | Florin et al. | 382/154 |

FOREIGN PATENT DOCUMENTS

| | | |
|---|---|---|
| JP | 11-126218 A | 5/1999 |
| JP | 11-514121 A | 11/1999 |
| JP | 2002-133399 A | 5/2002 |
| JP | 2007-80268 A | 3/2007 |
| WO | WO-98/05003 A1 | 2/1998 |
| WO | WO-2007/046172 A1 | 4/2007 |

OTHER PUBLICATIONS

Farid et al, Separating reflections from images by use of independent component analysis, J. Opt. Soc. Am. A/ vol. 16, No. 9/Sep. 1999.*

Mckeown et al, Independent Component Analysis of fMRI Data—Examining the Assumptions, Human Brain Mapping 6:368-372(1998) r.*

International Search Report for the Application No. PCT/JP2008/050266 mailed Apr. 15, 2008.

Chen, Yen-Wei, "Independent Component Analysis(1) -Cocktail Party Effect-", Medical Imaging Technology, 2003, vol. 21, No. 1, pp. 81-85.

Chen, Yen-Wei, "Independent Component Analysis (2)-Feature Extractions based on ICA Basis Functions-", Medical Imaging Technology, 2003, vol. 21, No. 2, pp. 170-174.

Murata, Noboru, "Introduction—Independent Component Analysis", Tokyo Denki University Press, 2004, pp. 66-71.

Hyvärinen, Aapo et al., "Independent Component Analysis", Tokyo Denki University Press, 2005, pp. 206-213.

The Second Office Action for the Application No. 200880124307.5 from The State Intellectual Property Office of the People's Republic of China dated Mar. 7, 2012.

Chen, Yen-Wei et al., "ICA Domain Filtering for Reduction of Noise in X-ray Images", Medical Imaging 2006, Proceedings of SPIE, vol. 6144, pp. 614469-1 to 614469-8.

* cited by examiner

IMAGE PROCESSING METHOD, AN APPARATUS THEREFOR AND A TOMOGRAPHIC APPARATUS FOR REMOVING ARTIFACTS FROM A SECTIONAL IMAGE

TECHNICAL FIELD

This invention relates to an image processing method for sectional images, an apparatus therefor and a tomographic apparatus, and more particularly to a technique for removing artifacts.

BACKGROUND ART

A sectional image will be described taking for example a CT image obtained from an X-ray CT (Computed Tomography) apparatus which picks up images by revolving an imaging system including an X-ray tube (emitting device) and a detector (detecting device) about the body axis of a patient. X-ray CT apparatus are medical equipment indispensable to clinical practice, and include a single slice CT apparatus, a multi-slice CT apparatus with detector cells juxtaposed along the direction of a body axis, and a cone-beam CT apparatus which emits a cone-shaped X-ray beam spreading along the direction of a body axis from an X-ray tube. As a detector provided for an X-ray CT apparatus, a flat panel X-ray detector (hereinafter abbreviated as "FPD") has recently been used in cone-beam CT.

In the case of an X-ray CT apparatus, with the imaging system revolved about the body axis of a patient, an artifact appears in a ring shape on a CT image (hereinafter abbreviated as "ring artifact"). This will particularly be described with reference to FIG. 14. FIG. 14 is a schematic view for use in description of ring artifact generation on a CT image. In FIG. 14, a single slice CT apparatus will be described by way of example, for the sake of brief description. Generally, a ring artifact is generated on a CT image by deficiency or sensitivity degradation of a cell (see the cell affixed with sign "D" in FIG. 14(a)) of a detector which is represented by an X-ray detecting array 4, for example. By revolving a channel detector in one row and an X-ray tube 2 forming a pair about the body axis z of a patient M, original data (called "sinogram") is acquired which, as shown in FIG. 14(b), has a horizontal axis representing the direction of arrangement of the cells of the channel detector (also called "Channel direction"), and a vertical axis representing the direction of projection (also called "View direction"). When a certain cell of the detector has deficiency or sensitivity variation D as shown in FIG. 14(a), a linear artifact $ART_1$ will appear on the sinogram and, as shown in FIG. 14(c), a ring-like artifact (ring artifact) $ART_2$ will appear on a reconstructed CT image. Even a sensitivity difference of only 0.1% of the detector can become clearly visible as a ring.

Conventionally, it has been general practice to remove ring artifacts on CT images by interpolating a deficient pixel on a sinogram, or through a sensitivity correction of the detector. On the other hand, there are Patent Documents 1 and 2 as a technique of removing ring artifacts by processing on CT images. In Patent Documents 1 and 2, a distribution of variations in the belt-like width of the ring or luminance (pixel value) is checked beforehand by collecting and observing ring artifacts on the CT images. A lowpass filter (low-pass type filter), a median filter or the like is applied directly to the ring artifacts meeting these conditions, thereby to remove the ring artifacts.

Incidentally, Independent Component Analysis (ICA) has been proposed as a multi-dimension signal analyzing method in recent years, which observes mixed signals having independent signals overlapping one another, and separates them into independent original signals (see Nonpatent Documents 1-5, for example). Nonpatent Document 2, in particular, applies Independent Component Analysis (ICA) to an image, and develops the image with a basis function, to calculate a characteristic vector and analyzes the characteristic of the image.

[Patent Document 1]
Patent National Publication H11-514121
[Patent Document 2]
Unexamined Patent Publication H11-128218 [Nonpatent Document 1]
Chin En-i, "Independent Component Analysis (1)—Cocktail Party Effect—", Japanese Society of Medical Imaging Technology, 2003, Vol. 21, No. 1, p. 81-85
[Nonpatent Document 2]
Chin En-i, "Independent Component Analysis (2)—Characteristic Extraction by ICA base—", Japanese Society of Medical Imaging Technology, 2003, Vol. 21, No. 2, p. 170-174
[Nonpatent Document 3]
Noboru Murata, "Introduction—Independent Component Analysis", Tokyo Denki University Press, July, 2004
[Nonpatent Document 4]
Aapo Hyvarinen, Juha Karhunen & Erkki Oja, translated by Chikashi Nemoto & Masayoshi Kawato "Detailed Description: Independent Component Analysis—New World of Signal Analysis—" Tokyo Denki University Press, February, 2005
[Nonpatent Document 5]
Murata Noboru, "An Introduction to Independent Component Analysis", May 1, Heisei 14, Waseda University, Department of Science and Engineering, Faculty of Electric, electronics and information engineering, [online] Internet <URL: http://www.eb.waseda.ac.jp/murata/~mura/lecture/ica/note/>

DISCLOSURE OF THE INVENTION

Problem to be Solved by the Invention

However, each individual detector is slightly different in characteristic from another, and the sensitivity of a detector may change in time. It is difficult to remove artifacts completely only by sensitivity process of a sinogram noted hereinbefore. Further, the strength of artifacts may vary between areas (e.g. the upper half and the lower half) on a CT image. This can be dealt with more easily on the image than on the sinogram. As in Patent Documents 1 and 2, direct application of a filter to an image for the purpose of smoothing as noted hereinbefore will lower resolution of an original CT image, and may generate artifacts due to the filter.

This invention has been made having regard to the state of the art noted above, and its object is to provide an image processing method, an apparatus therefor and a tomographic apparatus, which are capable of removing artifacts stably.

Means for Solving the Problem

To fulfill the above object, this invention provides the following construction.

An image processing method of this invention is an image processing method for processing a sectional image, wherein the sectional image is divided into a pixel group including artifacts and a pixel group without the artifacts by carrying out a feature quantity analysis of the artifacts, and a correction process is carried out to remove the artifacts by performing a predetermined process relating to correction only with respect to the pixel group including the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without the artifacts.

According to the image processing method of this invention, a sectional image is divided into a pixel group including artifacts and a pixel group not including artifacts by carrying out a feature quantity analysis of the artifacts, and a predetermined process relating to correction is performed only with respect to the above pixel group including the artifacts, thereby to carry out a correction process for removing the artifacts. Thus, the predetermined process relating to correction is performed only with respect to the pixel group including the artifacts, and the predetermined process relating to correction is not performed with respect to the pixel group not including the artifacts. A filtering process or the like for correction is not performed with respect to a proper, normal sectional image formed of the pixel group not including the artifacts. Artifacts due to a filter are not generated, and there hardly occur any side effects due to the filter such as a reduction in image resolution. As a result, the artifacts can be removed stably. The clause in this specification, the "predetermined process relating to correction is performed only with respect to the pixel group including the artifacts" only means that the predetermined process relating to correction is not performed with respect to the pixel group not including the artifacts. It should be noted that predetermined processes not relating to correction (e.g. a scale transform from pixel value to luminance, and correction processes other than artifact removal (for example, lag correction and gain correction)) may be performed with respect to the pixel group not including the artifacts.

The above feature quantity analysis is an independent component analysis. Using the independent component analysis, a separation is made independently into image components corresponding to the artifacts and image components not corresponding to the artifacts, thereby dividing into the pixel group including the artifacts and the pixel group without the artifacts. The feature quantity analysis is not limited to the independent component analysis, but may be wavelet conversion, for example. When the independent component analysis is used as feature quantity analysis, more specifically the following process may be carried out.

For example, the predetermined process relating to correction is performed only with respect to the pixel group including the artifacts by eliminating image components corresponding to the artifacts. The image components corresponding to the artifacts may be eliminated as follows.

For example, with a sectional plane of the sectional image regarded as an x, y plane, and each pixel value of the sectional image regarded as F (x, y), the sectional image F (x, y) is divided by the x, y into groups, Δ in number, thereby to obtain images $F_i$ (x, y) (where i=1 to Δ) formed of N pixels, and by applying the independent component analysis, each element image $F_i$ (x, y) is developed with basis functions $A_j$ consisting of N pixels (where j=1 to N), as in;

$$F_i(x,y) = \Sigma_{j=1}^{N} s_{ji} * A_j \quad (A).$$

Basis function(s) $A_h$ (where 1≦h≦N; the number of applicable h being one or more) corresponding to the artifacts is/are selected from among the basis functions $A_j$ developed by equation (A) above, components $s_{hi}$ corresponding to the selected basis function(s) $A_h$ being regarded as image components corresponding to the artifacts. The correction process is carried out on each of the element images $F_i$ (x, y), which replaces the components $s_{hi}$ with "0", thereby eliminating the image components corresponding to the artifacts. The element images $F_i$ (x, y) are arranged by i=1 to Δ, thereby obtaining a sectional image without the artifacts. The basis function(s) $A_h$ corresponding to the artifacts is/are not limited to one, but there may be a plurality of basis functions $A_h$ corresponding to the artifacts. In this case, the artifacts can be removed by replacing all the corresponding components $s_{hi}$ with "0".

For example, the above sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the r, θ into groups, Δ in number, thereby to obtain images $F_i$ (r, θ) (where i=1 to Δ) formed of N pixels. By applying the above independent component analysis, each element image $F_i$ (r, θ) is developed with basis functions $A_j$ consisting of N pixels (where j=1 to N), as in;

$$F_i(r,\theta) = \Sigma_{j=1}^{N} s_{ji} * A_j \quad (B)$$

Basis function(s) $A_h$ (where 1≦h≦N; the number of applicable h being one or more) corresponding to the artifacts is/are selected from among the basis functions $A_j$ developed by equation (B) above, components $s_{hi}$ corresponding to the selected basis function(s) $A_h$ being regarded as image components corresponding to the artifacts. The correction process is carried out on each of the element images $F_i$ (r, θ), which replaces the components $s_{hi}$ with "0", thereby eliminating the image components corresponding to the artifacts. An image F (r, θ) having the element images $F_i$ (r, θ) arranged by i=1 to Δ is inverse transformed to a sectional image F (x, y) on rectangular coordinates of rectangular coordinate system x, y, thereby obtaining a sectional image without the artifacts. In this example also, the basis function(s) $A_h$ corresponding to the artifacts is/are not limited to one, but there may be a plurality of basis functions $A_h$ corresponding to the artifacts. In this case, the artifacts can be removed by replacing all the corresponding components $s_{hi}$ with "0". When the sectional image is a CT image, the sectional image F (x, y) is transformed to image F (r, θ) on the polar coordinates of polar coordinate system r, θ, thereby to transform ring artifacts on sectional image F (x, y) to linear artifacts on the image F (r, θ).

When the independent component analysis is used as feature quantity analysis, it is preferred that the predetermined process relating to correction is performed only with respect to the pixel group including the artifacts by applying a smoothing filter to the pixel group including the artifacts. Compared with the above technique of using the independent component analysis for eliminating the image components corresponding to the artifacts, side effects due to the filter, such as a reduction in image resolution, on a proper, normal sectional image can be further inhibited.

The case of applying the smoothing filter to the pixel group including the artifacts may be summarized as follows. That is, using the independent component analysis, a separation is made independently into image components corresponding to the artifacts and image components not corresponding to the artifacts, thereby dividing into an image group including the artifacts and an image group not including the artifacts. Then, the smoothing filter noted above is applied to the image components corresponding to the artifacts, thereby performing the predetermined process relating to correction only with respect to the pixel group including the artifacts. The smoothing filter may be applied to the image components corresponding to the artifacts as follows.

That is, basis function(s) $A_h$ (where $1 \leq h \leq N$; the number of applicable h being one or more) corresponding to artifacts is/are selected from among the basis functions $A_j$ developed by equation (B) above. Element images $s_{hi}*A_h$ consisting of the selected basis function(s) $A_h$ and components $s_{hi}$ corresponding thereto are regarded as image components corresponding to the artifacts. A correction process is carried out on the element images $F_h$ (r, θ) consisting of $s_{hi}*A_h$, which smoothes the image components corresponding to the artifacts by applying the smoothing filter to the image components. An image F (r, θ) having the element images $F_h$ (r, θ), and the element images $F_i$ (r, θ) consisting of the remaining basis functions $A_j$ not selected and components $s_{ji}$ corresponding thereto, which are arranged by i=1 to Δ, is inverse transformed to sectional image F (x, y) on the rectangular coordinates of rectangular coordinate system x, y, thereby obtaining a sectional image without the artifacts. More specifically, the following process may be carried out in such a case.

For example, the element images $F_h$ (r, θ) consisting of the element images $s_{hi}*A_h$ are divided by the θ into images $F_{hk}$ (r, θ) (where k=1 to M) of M areas (where M is a natural number including 1), a profile function $P_k(r)$ of each of the images $F_{hk}$ (r, θ) integrated with θ is obtained. $P_k(r)'$ is obtained by applying the smoothing filter about the r to the profile function $P_k(r)$, a correction is made by substituting images $F_{hk}$ (r, θ) into the right-hand side of the following equation (C):

$$F_{hk}(r,\theta)=F_{hk}(r,\theta)*P_k(r)'/P_k(r) \quad (C)$$

and finding a solution to the left-hand side, and the element images $F_h$ (r, θ) are corrected by arranging the corrected images $F_{hk}$ (r, θ) by k=1 to M. Since M is a natural number including 1 here, the case is also included where element images $F_h$ (r, θ) are corrected by substituting the element images $F_h$ (r, θ), without being divided, into the right-hand side of equation (C) above and finding a solution to the left-hand side.

When the strength of the artifacts varies in the areas on the above CT image, this can be dealt with by appropriately adjusting the value of this M for use.

For example, a correction is made also by substituting images $F_{hk}$ (r, θ) into the right-hand side of the following equation (D):

$$F_{hk}(r,\theta)=F_{hk}(r,\theta)-(P_k(r)-P_k(r)') \quad (D)$$

and finding a solution to the left-hand side, and the element images $F_h$ (r, θ) are corrected by arranging the corrected images $F_{hk}$ (r, θ) by k=1 to M. In this example also, the case is also included where element images $F_h$ (r, θ) are corrected by substituting the element images $F_h$ (r, θ), without being divided, into the right-hand side of equation (D) above and finding a solution to the left-hand side. Generally, when the value of profile function $P_k(r)$ can be extremely smaller than the value of $P_k(r)'$ resulting from the smoothing, the division as in equation (C) above could increase the influence of noise. Thus, a subtraction as in the following equation (D) is more advantageous.

These inventions described above are premised on the technical idea of carrying out a correction process to remove artifacts, by performing a feature quantity analysis of the artifacts to make a division into a pixel group including the artifacts and a pixel group not including the artifacts, and performing a predetermined process relating to correction only with respect to the above pixel group including the artifacts. Instead of being premised on such technical idea, the smoothing filter may be applied to the sectional image by transforming equation (C) above into the following equation (C)' or transforming equation (D) above into the following equation (D)'.

An image processing method different from the above image processing method is an image processing method for processing a sectional image, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the θ into images $F_k$ (r, θ) (where k=1 to M) of M areas (where M is a natural number including 1), a profile function $P_k(r)$ of each of the images $F_k$(r, θ) integrated with θ is obtained, $P_k(r)'$ is obtained by applying a smoothing filter about the r to the profile function $P_k(r)$, a correction is made by substituting images $F_k$ (r, θ), using $P_k(r)'$ obtained, into the right-hand side of the following equation (C)':

$$F_k(r,\theta)=F_k(r,\theta)*P_k(r)'/P_k(r) \quad (C)'$$

and finding a solution to the left-hand side, the image F (r, θ) is corrected by arranging the corrected images $F_k$ (r, θ) by k=1 to M, and this image F (r, θ) is inverse transformed to a sectional image F (x, y) on rectangular coordinates of rectangular coordinate system x, y, thereby obtaining a sectional image without the artifacts.

Another image processing method different from the above image processing method is an image processing method for processing a sectional image, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the θ into images $F_k$ (r, θ) (where k=1 to M) of M areas (where M is a natural number including 1), a profile function $P_k(r)$ of each of the images $F_k$ (r, θ) integrated with θ is obtained, $P_k(r)'$ is obtained by applying a smoothing filter about the r to the profile function $P_k$ (r), a correction is made by substituting images $F_k$ (r, θ), using $P_k(r)'$ obtained, into the right-hand side of the following equation (D)':

$$F_k(r,\theta)=F_{hk}(r,\theta)-(P_k(r)-P_k(r)') \quad (D)'$$

and finding a solution to the left-hand side, the image F (r, θ) is corrected by arranging the corrected images $F_k$ (r, θ) by k=1 to M, and this image F (r, θ) is inverse transformed to a sectional image F (x, y) on rectangular coordinates of rectangular coordinate system x, y, thereby obtaining a sectional image without the artifacts.

The following can be said also of equation (C)' above and equation (D)' above. Generally, when the value of profile function $P_k(r)$ can be extremely smaller than the value of $P_k(r)'$ resulting from the smoothing, the subtraction as in the equation (D)' is more advantageous than equation (C)' above.

In these inventions described above, one example of the sectional image is an image obtained by an imaging system revolving about and relative to a body axis of a patient (i.e. a CT image). When the sectional image is a CT image, artifacts appear as ring artifacts on the CT image by revolving the imaging system about the body axis of the patient. In these inventions, the sectional image which is a CT image is particularly useful. The sectional image is not limited to a CT image, but may be any image obtainable by tomography. There is no limitation regarding the sectional image, as exemplified by a sectional image obtained by an emitting device of the imaging system moving parallel to the patient and a detecting device of the imaging system moving parallel in a direction opposite to the movement of the emitting device, and a sectional image obtained by the imaging system making precession movement about an axis extending perpendicular to the body axis of the patient.

An image processing apparatus of this invention is an image processing apparatus for processing a sectional image, comprising a dividing device for dividing the sectional image into a pixel group including artifacts and a pixel group without the artifacts by carrying out a feature quantity analysis of the artifacts, and a pixel group processing device for performing a predetermined process relating to correction only with respect to the pixel group including the artifacts, whereby a correction process is carried out to remove the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without the artifacts.

According to the image processing apparatus of this invention; a correction process is carried out to remove the artifacts, with the dividing device dividing the sectional image into a pixel group including artifacts and a pixel group not including artifacts by carrying out a feature quantity analysis of the artifacts, and the pixel group processing device performing the predetermined process relating to correction only with respect to the above pixel group including the artifacts. Thus, the predetermined process relating to correction is performed only with respect to the pixel group including the artifacts, and the predetermined process relating to correction is not performed with respect to the pixel group not including the artifacts. A proper, normal sectional image formed of the pixel group not including the artifacts has hardly any side effects due to a filter such as a reduction in image resolution, and the artifacts can be removed stably. With the artifacts removed stably, an excellent sectional image can be obtained.

Using the independent component analysis, a separation is made independently into image components corresponding to the artifacts and image components not corresponding to the artifacts, thereby dividing into the pixel group including the artifacts and the pixel group without the artifacts.

As noted also in the image processing method, the sectional image is an image obtained by an imaging system revolving about and relative to a body axis of a patient (i.e. a CT image). Similarly, the sectional image is not limited to a CT image.

Further, a tomographic apparatus of this invention is a tomographic apparatus for imaging a sectional image, comprising a detecting device for detecting light or radiation from a patient, and an image processing device for processing the sectional image of the patient relating to the light or radiation obtained by the detecting device, wherein the image processing device includes a dividing device for dividing the sectional image into a pixel group including artifacts and a pixel group without the artifacts by carrying out a feature quantity analysis of the artifacts, and a pixel group processing device for performing a predetermined process relating to correction only with respect to the pixel group including the artifacts, whereby a correction process is carried out to remove the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without the artifacts.

According to the tomographic apparatus of this invention, the detecting device detects light or radiation from a patient, and the image processing device processes a sectional image of the patient relating to the light or radiation obtained by the detecting device, thereby picking up the sectional image. This image processing device carries out a correction process to remove artifacts, with the dividing device dividing the sectional image into a pixel group including artifacts and a pixel group not including artifacts by carrying out a feature quantity analysis of the artifacts, and the pixel group processing device performing the predetermined process relating to correction only with respect to the above pixel group including the artifacts. Thus, the predetermined process relating to correction is performed only with respect to the pixel group including the artifacts, and the predetermined process relating to correction is not performed with respect to the pixel group not including the artifacts. A proper, normal sectional image formed of the pixel group not including the artifacts has hardly any side effects due to a filter such as a reduction in image resolution, and the artifacts can be removed stably. With the artifacts removed stably, an excellent sectional image can be obtained, and consequently excellent imaging can be carried out.

Using the independent component analysis, a separation is made independently into image components corresponding to the artifacts and image components not corresponding to the artifacts, thereby dividing into the pixel group including the artifacts and the pixel group without the artifacts.

The above tomographic apparatus may comprise, besides the detecting device, an emitting device for emitting the light or radiation toward the patient. In this case, the detecting device detects the light or radiation transmitted through the patient. The invention may of course be applied to an apparatus, such as a nuclear medical diagnostic apparatus in which, instead of having an emitting device, a radioactive substance is introduced into the body of a patient, and the detecting device detects radiation (e.g. α-rays, β-rays or γ-rays) generated from the patient, thereby obtaining sectional images.

The tomographic apparatus is useful when comprising a revolving device for revolving the emitting device and the detecting device about and relative to the body axis of the patient, wherein the sectional image is an image (CT image) obtained by the emitting device and the detecting device revolving about and relative to a body axis of the patient. As noted also in the image processing method and the apparatus therefor, the tomographic apparatus is not limited to an X-ray CT apparatus, and the sectional image is not limited to a CT image, either.

Effects Of The Invention

With the image processing method, the apparatus therefor and the tomographic apparatus according to this invention, a sectional image is divided into a pixel group including artifacts and a pixel group not including artifacts by carrying out a feature quantity analysis of the artifacts, and a predetermined process relating to correction is performed only with respect to the above pixel group including the artifacts, thereby to carry out a correction process for removing the artifacts. Thus, the predetermined process relating to correction is performed only with respect to the pixel group including the artifacts, and the predetermined process relating to correction is not performed with respect to the pixel group not including the artifacts. A proper, normal sectional image formed of the pixel group not including the artifacts has hardly any side effects due to a filter such as a reduction in image resolution, and the artifacts can be removed stably.

Using the independent component analysis, a separation is made independently into image components corresponding to the artifacts and image components not corresponding to the artifacts, thereby dividing into the pixel group including the artifacts and the pixel group without the artifacts.

DESCRIPTION OF REFERENCES

| [Description of References] | |
|---|---|
| 2 | X-ray tube |
| 3 | X-ray detecting elements |
| 4 | X-ray detecting array |
| 5 | revolving unit |
| 8 | image processor |
| 8b | dividing unit |
| 8c | pixel group processing unit |
| F (x, y) | sectional images |
| $A_j$ | basis functions |
| $F_i(x, y)$, $F_i(r, \theta)$ | element images |
| z | body axis |
| M | patient |

Embodiment 1

Figure 1:
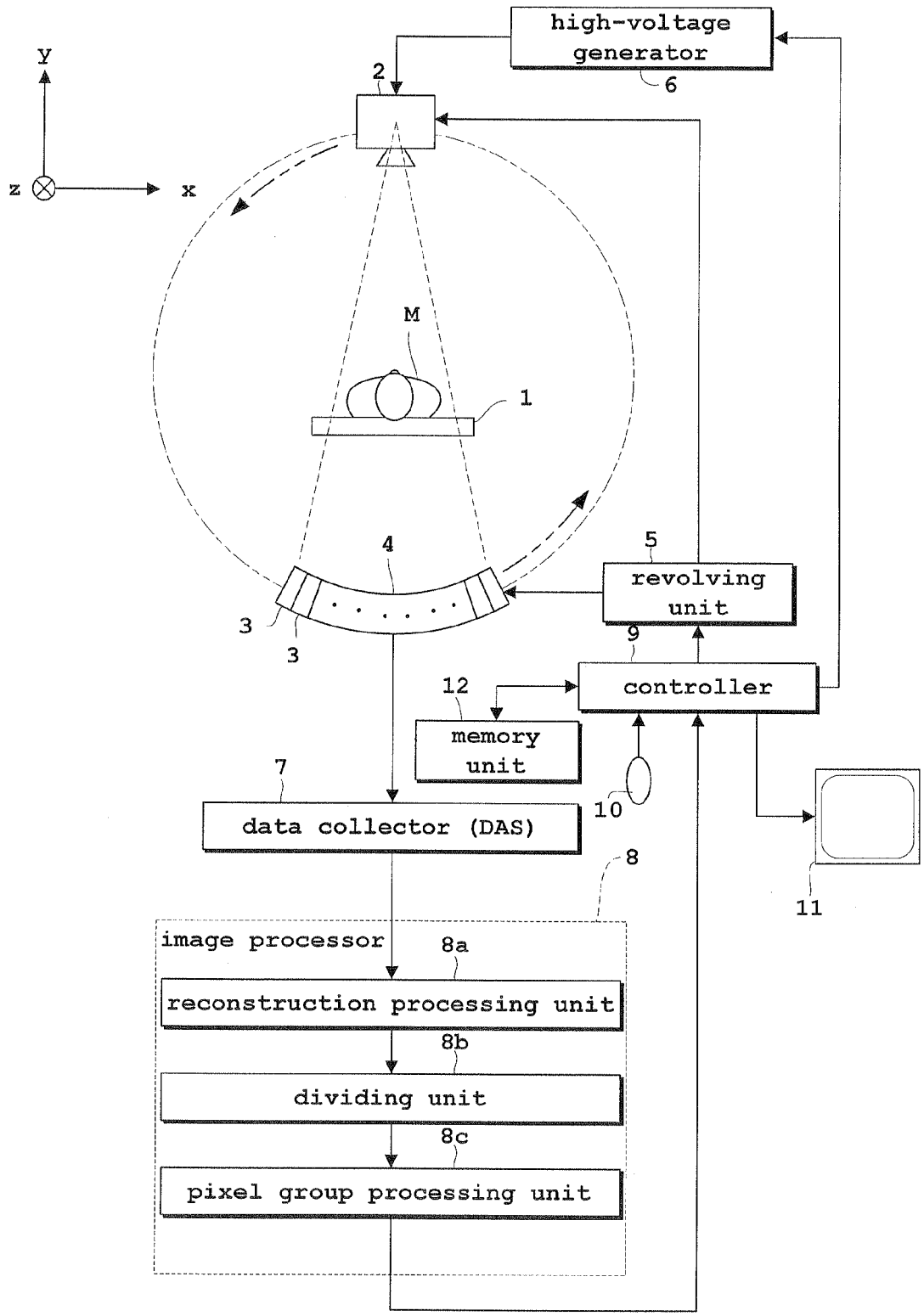
FIG. 1 is an outline view and block diagram of an X-ray CT apparatus according to each embodiment.
Figure 2:
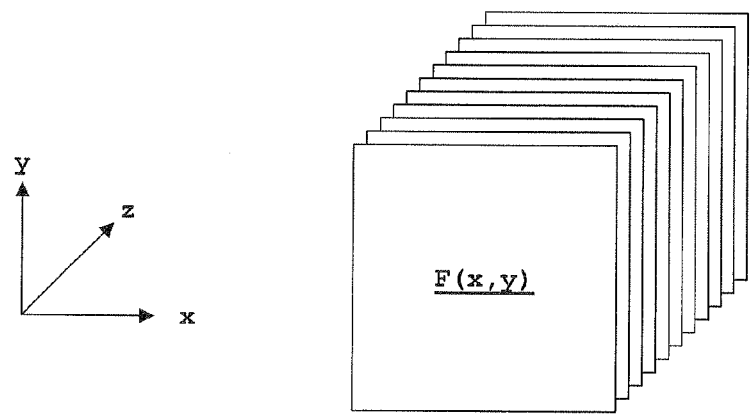
FIG. 2 is a schematic view for use in description of acquisition of each sectional image.
Figure 3:
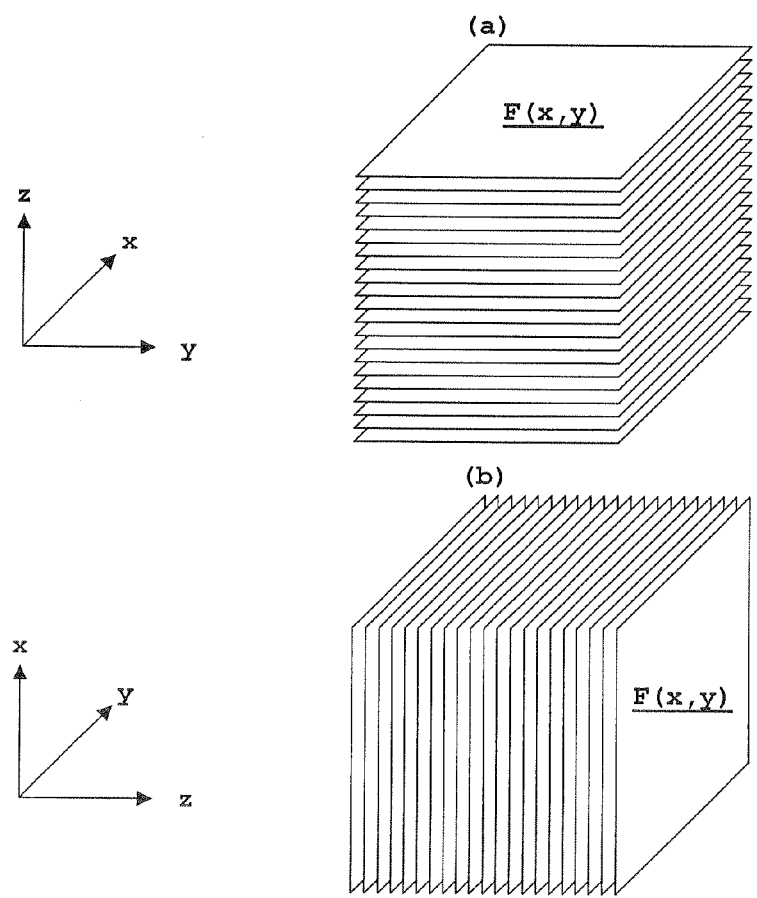
FIGS. 3(a) and (b) are schematic views of a rectangular coordinate system and each sectional image when x, y and z are changed, respectively.

Embodiment 1 of this invention will be described hereinafter with reference to the drawings. FIG. 1 is an outline view and block diagram of an X-ray CT apparatus according to each embodiment, including also Embodiments 2 and 3 to follow. FIG. 2 is a schematic view for use in description of acquisition of each sectional image. FIG. 3 is a schematic view of a rectangular coordinate system and each sectional image when x, y and z are changed, respectively. In this Embodiment 1, including also Embodiments 2 and 3 to follow, an X-ray CT apparatus will be described as an example of tomographic apparatus, and CT images will be described as an example of sectional images.

As shown in FIG. 1, the body axis of a patient M is regarded as z which is a direction normal to the plane of the drawing. X-axis and y-axis are set as shown in FIG. 1. The X-ray CT apparatus according to this Embodiment 1, including also Embodiments 2 and 3 to follow, as shown in FIG. 1, includes a top board 1 for supporting the patient M, an X-ray tube 2 for emitting X-rays toward the patient M, and an X-ray detecting array 4 for detecting X-rays transmitted through the patient M. The X-ray tube 2 is constructed to emit X-rays in a fan shape. In the case of cone-beam CT, the X-ray tube 2 emits a cone-shaped X-ray beam spreading along the direction of body axis z. X-ray detecting elements 3 are constructed as cells of a channel as a unit, which are arranged in a ring shape to constitute the X-ray detecting array 4. In the case of multi-slice CT, the X-ray detecting array 4 has X-ray detecting elements 3 arranged also along the direction of body axis z. In the case of cone-beam CT, an FPD having X-ray detecting elements 3 arranged two-dimensionally on a flat panel is used as the X-ray detecting array 4. The X-ray tube 2 corresponds to the emitting device in this invention. The X-ray detecting array 4 corresponds to the detecting device in this invention.

The X-ray CT apparatus includes a revolving unit 5 for revolving an imaging system consisting of the X-ray tube 2 and X-ray detecting array 4 about the body axis z of the patient M. This revolving unit 5 has a motor, a rotation belt and so on not shown, wherein rotation of the motor rotates the rotation belt. A gantry (not shown) is rotatable by rotation of the rotation belt, whereby the X-ray tube 2 and X-ray detecting array 4 arranged in the gantry revolve, as opposed to each other, in the direction of arrows in the figure, or in the opposite direction. The revolving unit 5 corresponds to the revolving device in this invention.

In addition, the X-ray CT apparatus includes a high-voltage generator 6 which applies a tube current or a tube voltage of high voltage to the X-ray tube 2, a data collector (DAS) 7 for collecting data obtained by the X-ray detecting array 4 as projection data, an image processor 8 for executing various processes on the projection data collected by the data collector 7, a controller 9 for performing overall control of the components of the X-ray CT apparatus, an input unit 10 for making inputs to the controller 9, an output unit 11 for outputting various data fed through the controller 9, and a memory unit 12 for writing and storing various data fed through the controller 9. The image processor 8 corresponds to the image processing apparatus in this invention, and corresponds also to the image processing device in this invention.

The controller 9 is formed of a central processing unit (CPU) and others. The input unit 10 feeds data and commands inputted by the operator to the controller 9. The input unit 10 has a pointing device represented by a mouse, keyboard, joystick, trackball and/or touch panel. The output unit 11 is formed of a display represented by a monitor, and/or a printer.

The memory unit 12 is formed of a storage medium represented by a ROM (Read-only Memory), a RAM (Random-Access Memory) and the like. In Embodiment 1, including also Embodiments 2 and 3 to follow, data collected by the data collector 7 and various data processed by the image processor 8 are written and stored in the RAM, and are read from the RAM as necessary. The ROM stores programs for carrying out various types of tomography. The controller 9 executes the programs to carry out the types of tomography corresponding to the programs, respectively.

The data collector 7 and image processor 8 are realized by the controller 9 executing, for example, the programs stored in the ROM of the storage medium represented by the above memory unit 12, or commands inputted with the pointing device represented by the input unit 10. The image processor 8 includes a reconstruction processing unit 8a for reconstructing the projection data collected by the data collector 7 to obtain sectional images (CT images here), a dividing unit 8b for dividing the sectional images into a pixel group including ring artifacts and a pixel group not including ring artifacts, and a pixel group processing unit 8c for performing a predetermined process relating to correction only with respect to the pixel group including ring artifacts. Specific functions of the dividing unit 8b and pixel group processing unit 8c will be described hereinafter with reference to FIGS. 4-6. The dividing unit 8b corresponds to the dividing device in this invention. The pixel group processing unit 8c corresponds to the pixel group processing device in this invention.

The reconstruction processing unit 8a carries out a reconstruction process based on the projection data to obtain sectional images. The reconstruction process may be carried out using the well-known filtered back projection (FBP) (also called "filter correcting back projection"). The sectional images obtained in this way are data obtained by revolving the X-ray tube 2 and X-ray detecting array 4 about the body axis z of the patient M, i.e. in the x, y plane in FIG. 1, and therefore their sectional plane is the x, y plane. Each pixel value of the sectional images is F (x, y).

In this Embodiment 1, including also Embodiments 2 and 3, x-, y- and z-axes are set as shown in FIG. 1, and therefore sectional images F (x, y) obtained are cross-sectional images, i.e. axial images. As shown in FIG. 2, axial images are obtained for respective sections (i.e. slices) in the direction of the body axis z. In this Embodiment 1, the sectional images F (x, y) are made axial images by setting x-, y- and z-axes as shown in FIG. 1. However, as shown in FIG. 3(a), the sectional images F (x, y) may be made coronal images by changing x in FIGS. 1 and 2 to y, changing y in FIG. 1 to z, and changing z in FIGS. 1 and 2 to x. Conversely, as shown in FIG. 3(b), the sectional images F (x, y) may be made sagittal images by changing x in FIGS. 1 and 2 to z, changing y in FIGS. 1 and 2 to x, and changing z in FIGS. 1 and 2 to y.

Figures 4, 5:
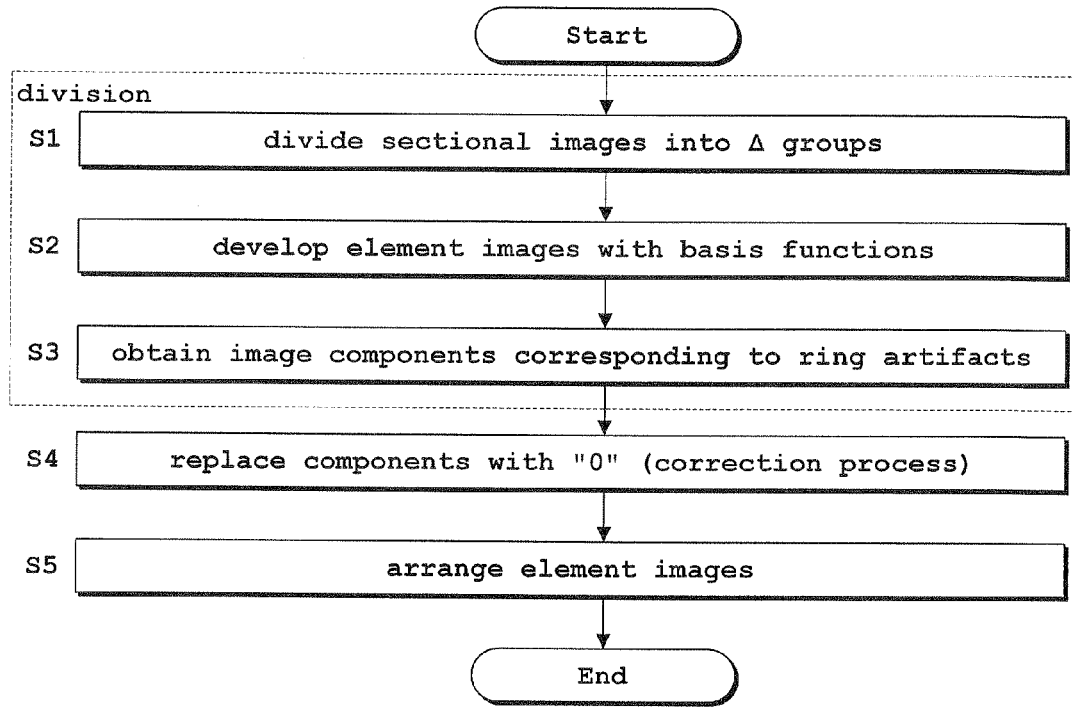
FIG. 4 is a flow chart showing a flow of a series of tomographic steps according to Embodiment 1.
FIG. 5 is a schematic view of element images acquired by dividing a single sectional image into 1024 groups.
Figure 6:
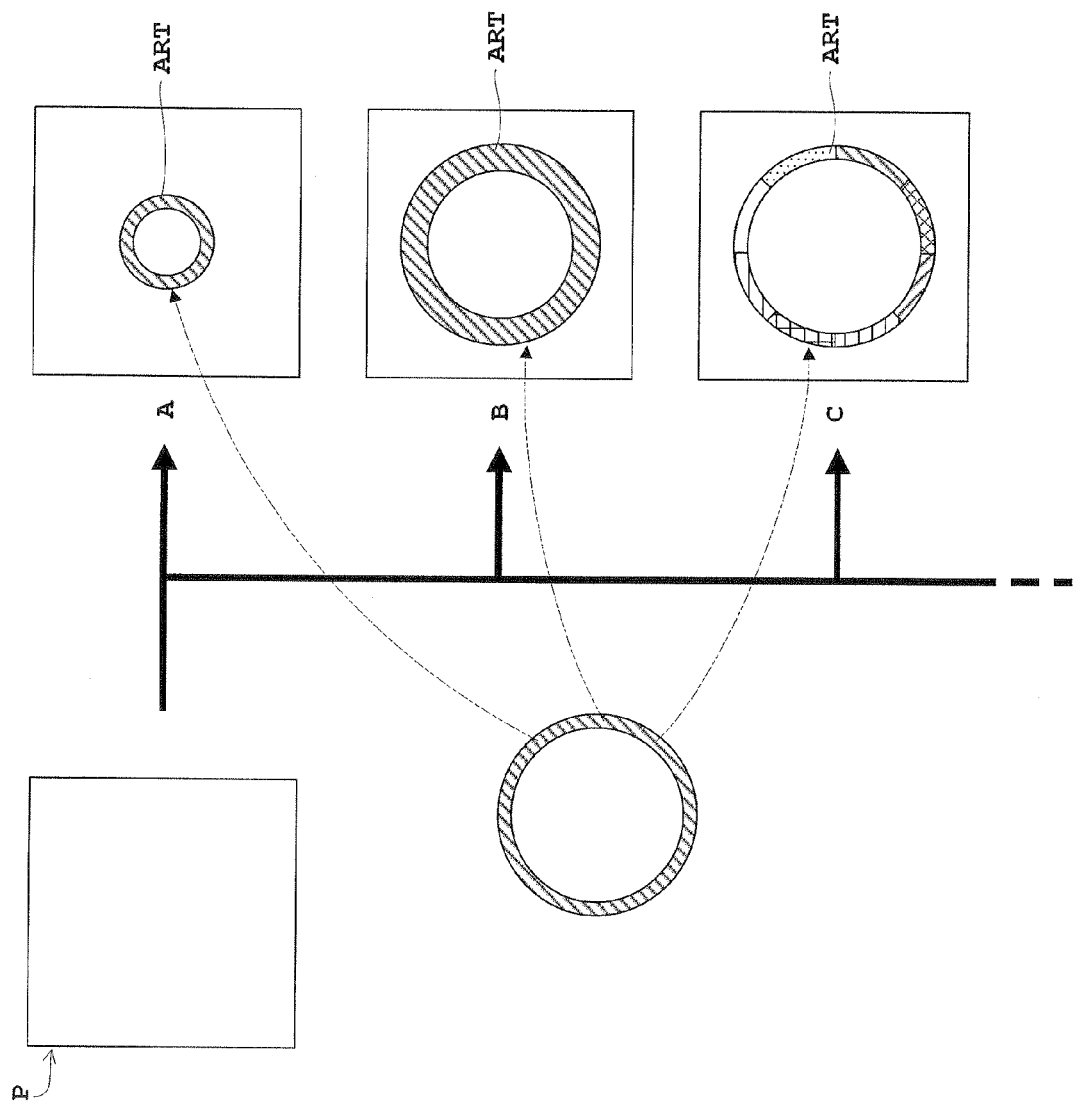
FIG. 6 is a schematic view of ring artifacts of various patterns artificially added to normal sectional images.

Therefore, the sectional images obtained as axial images may be transformed to coronal images or sagittal images. Since the X-ray CT apparatus revolves the X-ray tube 2 and X-ray detecting array 4 about the body axis z of the patient M (i.e. revolves them in the x, y plane in FIG. 1) as described above, ring artifacts will appear on the axial images. Therefore, from the viewpoint of removing the ring artifacts reliably, it is preferable that the sectional images F (x, y) are axial images. From the viewpoint of removing the ring artifacts reliably, it is preferable that, as described hereinafter, the sectional images obtained as axial images are, as remaining axial images, instead of being transformed to coronal images or sagittal images, divided into a pixel group including the ring artifacts and a pixel group not including the ring artifacts, Next, specific functions of the dividing unit 8b and pixel group processing unit 8c will be described with reference to FIGS. 4-6. FIG. 4 is a flow chart showing a flow of a series of tomographic steps according to Embodiment 1. FIG. 5 is a schematic view of element images acquired by dividing a single sectional image into 1024 groups. FIG. 6 is a schematic view of ring artifacts of various patterns artificially added to normal sectional images.

(Step S1) Divide Sectional Images into Δ Groups

The dividing unit 8b (see FIG. 1) divides sectional images F (x, y) into a pixel group including ring artifacts and a pixel group not including ring artifacts by analyzing the feature quantity of the ring artifacts. In this Embodiment 1, including also Embodiments 2 and 3 to follow, an independent component analysis (ICA) will be described as an example of the feature quantity analysis. By using the independent component analysis to separate independently image components corresponding to the ring artifacts, and image components not corresponding to the ring artifacts, the images are divided into an image group including the ring artifacts and an image group not including the ring artifacts. In this Embodiment 1, the sectional images F (x, y) are divided by x and y into groups, Δ in number, thereby to obtain images $F_i$ (x, y) (where i=1 to Δ) formed of N pixels.

Specifically, suppose sectional images F (x, y) which are also CT images, α in number, are obtained for respective slices in the direction of body axis z (see FIG. 2), basis functions $A_j$ formed of N pixels are calculated from the α sectional images F (x, y). Basis functions $A_j$ consist of $F_i$ (x, y) of N element pixels, and can be treated as vectors consisting of N elements. The number of basis functions $A_j$ is equal to the number of pixels forming the basis functions $A_j$ (j=1 to N). One sectional image F (x, y) has an arrangement, i=1 to Δ/α (where $\Delta_x \times \Delta_y = \Delta/\alpha$), of element images $F_i$ (x, y) belonging to groups of $\Delta_x$ and $\Delta_y$ in x- and y-directions, and is a set of Δ/α element images. Therefore, the α sectional images F (x, y) consist of Δ element images. The element images $F_i$ (x, y) consisting of N elements may also be treated as vectors consisting of N elements, and the α sectional images F (x, y) consist of Δ element images $F_i$ (x, y).

Description will be made here by taking, for example, a case where α=10, each sectional image F (x, y) has 512×512 pixels arranged longitudinally and transversely, N=256, $\Delta_x$=32 and $\Delta_y$=32 (that is, Δ/α=32×32=1024, Δ=1024×α=10240). Ten (α=10) sectional images F (x, y), each with 512×512 pixels, are acquired for respective slices in the direction of body axis z. Basis functions $A_j$ are formed of 16×16 pixels arranged longitudinally and transversely, i.e. 256 pixels (N=256), and can be treated as a vector consisting of 256 elements. The number (256 here) of basis functions $A_j$ is equal to the number of pixels forming the basis functions $A_j$ (j=1 to 256). As shown in FIG. 5, one sectional image F (x, y) has an arrangement, i=1 to 1024 (Δ/α=1024), of element images $F_i$ (x, y) belonging to groups, 1024 in total, of (512/16=) 32 ($\Delta_x$=32) and (512/16=) 32 ($\Delta_y$=32) in x- and y-directions, and is a set of 1024 element images. Therefore, ten sectional images F (x, y) have 10240 element images (A=10240). The element images $F_i$ (x, y) consisting of 256 pixels may also be treated as vectors formed of 256 elements. Ten sectional images F (x, y) have 10240 element images $F_i$ (x, y). Thus, one sectional image F (x, y) is divided into 1024 groups to obtain element images $F_i$ (x, y) consisting of 256 pixels. Ten sectional images F (x, y) are divided into 10240 groups to obtain element images $F_i$ (x, y) consisting of 256 pixels.

(Step S2) Develop Element Images with Basis Functions

Application of the independent component analysis will form a relational expression in the following equation (1) between each element image $F_i(x, y)$ and basis function $A_j$:

[Math 1]

$$[F_1(x, y), F_2(x, y), \Lambda, F_i(x, y), \Lambda, F_\Delta(x, y)] = [A_1, A_2, \Lambda, A_j, \Lambda, A_N] \cdot \begin{bmatrix} S_{11} & S_{12} & \Lambda & S_{1i} & \Lambda & S_{1\Delta} \\ S_{21} & S_{22} & \Lambda & S_{2i} & \Lambda & S_{2\Delta} \\ M & M & O & M & O & M \\ S_{j1} & S_{j2} & \Lambda & S_{ji} & \Lambda & S_{j\Delta} \\ M & M & O & M & O & M \\ S_{N1} & S_{N2} & \Lambda & S_{Ni} & \Lambda & S_{N\Delta} \end{bmatrix} \quad (1)$$

Equation (1) above is expressed by the product of a vector and a matrix, which is summarized into the following equation (2):

[Math 2]

$$F_i(x, y) = \sum_{j=1}^{N} S_{ji} * A_j \quad (2)$$

Where $i = 1$ to $\Delta$

The basis functions $A_j$ which satisfy equation (1) above or equation (2) above can be derived from application of the independent component analysis (ICA) noted hereinbefore. For a specific method of calculating basis functions $A_j$, see Nonpatent Document 1 (Chin En-i, "Independent Component Analysis (1)—Cocktail Party Effect—", Japanese Society of Medical Imaging Technology, 2003, Vol. 21, No. 1, p. 81-85) noted hereinbefore. Equation (1) above or equation (2) above corresponds to equation (A) in this invention.

(Step S3) Obtain Image Components Corresponding to Ring Artifacts

Basis function(s) $A_h$ (where $1 \leq h \leq N$; the number of applicable h being one or more) corresponding to the ring artifacts is/are selected from among the basis functions $A_j$ developed by equation (1) above or equation (2) above. Components $s_{hi}$ corresponding to the selected basis function(s) $A_h$ are regarded as the above-noted image components corresponding to the ring artifacts. The basis function(s) $A_h$ corresponding to the ring artifacts is/are not limited to one, but a plurality of basis functions $A_h$ exist.

For obtaining image components corresponding to the ring artifacts (i.e. components $s_{hi}$ corresponding to the selected basis function(s) $A_h$), as shown in FIG. 6, artifacts in various patterns (pattern A having a changed diameter of ring artifact ART, pattern B having a changed width of ring artifact ART and pattern C having a changed luminance (pixel value) or luminance distribution of ring artifact ART) are artificially added to normal sectional images P obtained beforehand. Sampling is carried out to check how each component $s_{ji}$ of the normal sectional images P is changed by the addition of the patterns. Image components $s_{hi}$ corresponding to the ring artifacts are obtained by preparing such sampling data beforehand. As another way of obtaining image components corresponding to the ring artifacts, image components $s_{hi}$ corresponding to an abnormal X-ray detecting array (i.e. ring artifacts) may be obtained, for example, by calculating sectional images, respectively, from an X-ray detecting array consisting only of normal cells and an X-ray detecting array having an abnormal cell, and obtaining image components corresponding to each sectional image. It is also possible to obtain image components $s_{hi}$ corresponding to the ring artifacts by calculating sectional images after multiplying a value of a particular cell of a sinogram acquired from an X-ray detecting array consisting only of normal cells, for example, by 0.99 (which corresponds to a reduction in the sensitivity of the particular cell to 99%).

With the image components $s_{hi}$ corresponding to the ring artifacts obtained in this way, element images $s_{hi}*A_h$ consisting of basis functions $A_h$ corresponding to the ring artifacts and components $s_{hi}$ corresponding thereto act as image components corresponding to the ring artifacts, i.e. a pixel group including the ring artifacts. And element images $s_{ji}*A_j$ consisting of the remaining basis function $A_j$ not selected and components $s_{ji}$ corresponding thereto act as image components not corresponding to the ring artifacts, i.e. a pixel group not including the ring artifacts. Therefore, through the steps in steps S1-S3, a division is made into the pixel group including the ring artifacts and the pixel group not including the ring artifacts. The dividing unit 8b noted above (see FIG. 1) executes the steps in steps S1-S3.

(Step S4) Replace Components with "0" (Correction Process)

The image components $s_{hi}$ corresponding to the ring artifacts obtained in step S3 are replaced with "0", thereby eliminating the image components $s_{hi}$ corresponding to the ring artifacts. That is, a correction process for the above elimination is carried out on each of the element images $F_i(x, y)$. Therefore, a predetermined process relating to correction is carried out only with respect to the pixel group including the ring artifacts by eliminating image components $s_{hi}$ corresponding to the ring artifacts. When a plurality of basis functions $A_h$ corresponding to the ring artifacts exist, all the corresponding image components $s_{hi}$ are replaced with "0". On the other hand, the image components not corresponding to the ring artifacts (the pixel group not including the ring artifacts) do not undergo a filtering process or the like for correction, let alone the correction process for replacement with "0" in this step S4. The above means only that the predetermined process relating to correction is not carried out on the pixel group not including the (ring) artifacts. Therefore, regarding predetermined processes not relating to correction (e.g. a scale transform from pixel value to luminance, and correction processes other than artifact removal (for example, lag correction, gain correction and so on)), such processes may be performed with respect to the pixel group not including the (ring) artifacts. The pixel group processing unit 8c noted above (see FIG. 1) carries out the correction process in this step S4.

(Step S5) Arrange Element Images

Element images $F_i(x, y)$ having undergone the correction process in step S4, and element images $F_i(x, y)$ consisting of the remaining basis functions $A_j$ not selected and components $s_{ji}$ corresponding thereto, are arranged by i=1 to Δ, thereby obtaining sectional images F (x, y) without the ring artifacts.

According to steps S1-S5 in this Embodiment 1, sectional images are divided into a pixel group including ring artifacts and a pixel group not including ring artifacts by carrying out a feature quantity analysis (independent component analysis (ICA) in this Embodiment 1) of the ring artifacts, and a correction process is carried out to remove the ring artifacts by performing the predetermined process relating to correction (process for replacing with "0" in this Embodiment 1) only with respect to the above pixel group including the ring artifacts. Thus, the predetermined process relating to correction is performed only with respect to the pixel group including the ring artifacts, and the predetermined process relating to correction is not performed with respect to the pixel group not including the ring artifacts. A filtering process or the like for correction is not performed for proper, normal sectional images formed of the pixel group not including the ring artifacts, and artifacts due to the filter are not generated and side effects due to the filter such as a reduction in image resolution are hardly produced. As a result, the artifacts (ring artifacts here) can be removed stably.

According to the image processor 8 in this Embodiment 1 and the X-ray CT apparatus having the same, the X-ray tube 2 emits X-rays toward the patient M, the X-ray detecting array 4 detects X-rays transmitted through the patient M, and the image processor 8 processes sectional images of the patient M relating to the X-rays obtained by the X-ray detecting array 4, thereby picking up the sectional images. This image processor 8 carries out a correction process to remove the ring artifacts, with the dividing unit 8b dividing the sectional images into a pixel group including ring artifacts and a pixel group not including ring artifacts by carrying out a feature quantity analysis of the ring artifacts (independent component analysis (ICA) in this Embodiment 1), and the pixel group processing unit 8c performing the predetermined process relating to correction (process for replacing with "0" in this Embodiment 1) only with respect to the above pixel group including the ring artifacts. Thus, the predetermined process relating to correction is performed only with respect to the pixel group including the ring artifacts, and the predetermined process relating to correction is not performed with respect to the pixel group not including the ring artifacts. Proper, normal sectional images formed of the pixel group not including the ring artifacts have hardly any side effects due to a filter such as a reduction in image resolution, and the artifacts (ring artifacts here) can be removed stably. With the artifacts removed stably, excellent sectional images can be obtained, and consequently excellent imaging can be carried out.

In this Embodiment 1, including also Embodiments 2 and 3 to follow, application is made to the X-ray CT apparatus having the revolving unit 5 which revolves the X-ray tube 2 and X-ray detecting array 4 about the body axis z of patient M. In this X-ray CT apparatus, sectional images are useful at the time of images (i.e. CT images) produced by the X-ray tube 2 and X-ray detecting array 4 revolving about the body axis z of patient M. When the sectional images are CT images, artifacts appear as ring artifacts on the CT images by revolving the imaging system including the X-ray tube 2 and X-ray detecting array 4 about the body axis z of patient M.

This Embodiment 1, including also Embodiments 2 and 3 to follow, employs the independent component analysis (ICA) as feature quantity analysis. Using the independent component analysis, a separation is made independently into image components corresponding to the ring artifacts and image components not corresponding to the ring artifacts, thereby dividing into an image group including the ring artifacts and an image group not including the ring artifacts.

In this Embodiment 1, including also Embodiment 2 to follow, a predetermined process relating to correction is performed only with respect to the pixel group including the artifacts by eliminating image components $s_{hi}$ corresponding to the ring artifacts. Specifically, in this Embodiment 1, sectional images F (x, y) are divided by x, y into groups, Δ in number, thereby to obtain images $F_i$ (x, y) (where i=1 to Δ) formed of N pixels. By applying the independent component analysis, each element image $F_i$ (x, y) is developed with basis functions $A_j$ consisting of N pixels (where j=1 to N). Basis function(s) $A_h$ (where 1≦h≦N; the number of applicable h being one or more) corresponding to the ring artifacts is/are selected from among the basis functions $A_j$ developed by equation (1) above or equation (2) above. Components $s_{hi}$ corresponding to the selected basis function(s) $A_h$ are regarded as image components corresponding to the ring artifacts. A correction process is carried out on each of the element images $F_i$ (x, y), which replaces the components $s_{hi}$ with "0", thereby eliminating the image components $s_{hi}$ corresponding to the ring artifacts. The element images $F_i$ (x, y) are arranged by i=1 to Δ, thereby obtaining sectional images F (x, y) without the ring artifacts.

As noted hereinbefore, the basis function(s) $A_h$ corresponding to the ring artifacts is/are not limited to one, but there may be a plurality of basis functions $A_h$ corresponding to the artifacts. In this case, the ring artifacts can be removed by replacing all the corresponding components $s_{hi}$ with "0".

Embodiment 2

Figure 7:
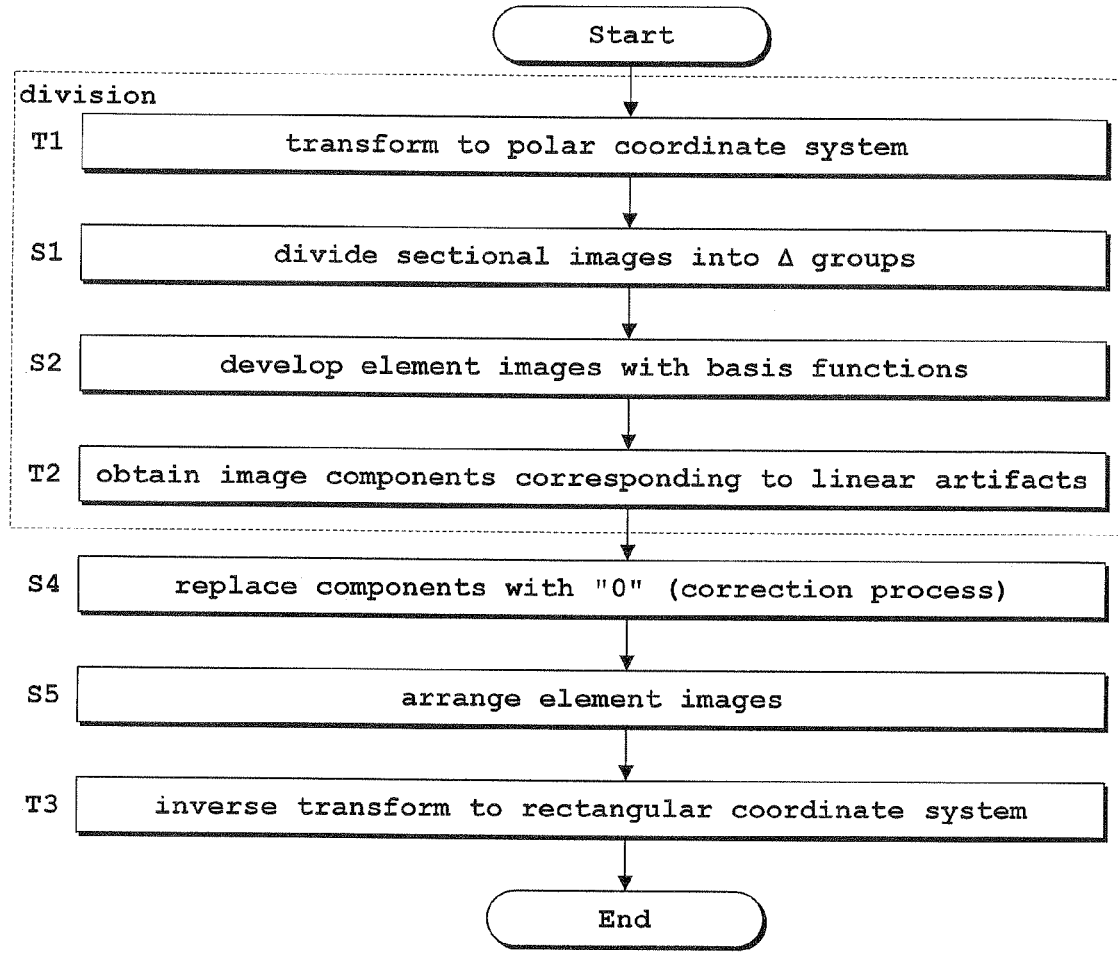
FIG. 7 is a flow chart showing a flow of a series of tomographic steps according to Embodiment 2.
Figure 8:
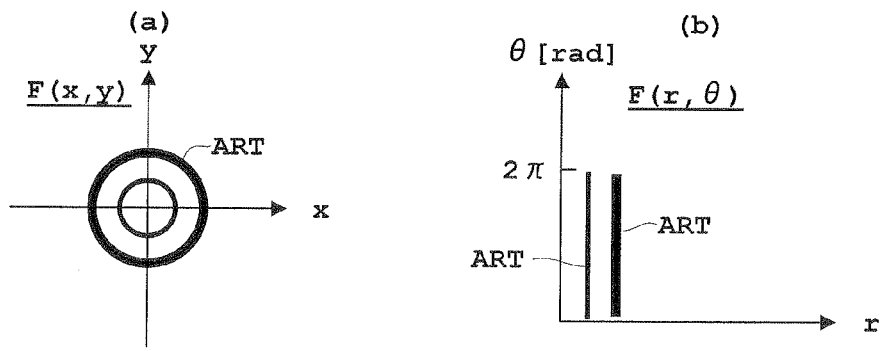
FIGS. 8(a) and (b) are schematic views showing a relationship of each sectional image and artifacts when transform is made from a rectangular coordinate system to a polar coordinate system.

Next, Embodiment 2 of this invention will be described with reference to the drawings. FIG. 7 is a flow chart showing a flow of a series of tomographic steps according to Embodiment 2. FIG. 8 is a schematic view showing a relationship of each sectional image and artifacts when transform is made from a rectangular coordinate system to a polar coordinate system. The X-ray CT apparatus according to this Embodiment 2 has the same construction as in foregoing Embodiment 1, and therefore its description will be omitted. In the flow chart of FIG. 7 according to Embodiment 2, the steps common to foregoing Embodiment 1 are affixed with the same signs, their description will be omitted, and only differences will be described.

(Step T1) Transform to Polar Coordinate System

The dividing unit 8b (see FIG. 1) transforms sectional images F (x, y) on rectangular coordinates of rectangular coordinate system x, y in FIG. 8(a) to image F (r, θ) on polar coordinates of polar coordinate system r, θ in FIG. 8(b). In this Embodiment 2, as in foregoing Embodiment 1 and Embodiment 3 to follow, CT images are employed as sectional images (x, y), and by transforming sectional images F (x, y) to images F (r, θ) on polar coordinates of the polar coordinate system r, θ, ring artifacts ART on sectional image F (x, y) shown in FIG. 8(a) are transformed to linear artifacts ART on image F (r, θ) shown in FIG. 8(b).

(Step S1) Divide Sectional Images into Δ Groups

This step S1 is the same as in Embodiment 1 except that the images to be divided are sectional images F (x, y) in Embodiment 1, but are images F (r, θ) in this Embodiment 2, and therefore its description is omitted. The images F (r, θ) are divided by r and θ into groups, Δ in number, thereby to obtain images $F_i$ (r, θ) (where i=1 to Δ) formed of N pixels.

(Step S2) Develop Element Images with Basis Functions

Application of the independent component analysis will form the following relational expression (3) between each element image $F_i$ (r, θ) and basis function $A_j$:

[Math 3]

$$F_i(r, \theta) = \sum_{j=1}^{N} S_{ji} * A_j \quad (3)$$

Where $i = 1$ to Δ

Equation (3) above corresponds to equation (B) in this invention.

(Step T2) Obtain Image Components Corresponding to Linear Artifacts

Basis function(s) $A_h$ (where $1 \leq h \leq N$; the number of applicable h being one or more) corresponding to linear artifacts is/are selected from among the basis functions $A_j$ developed by equation (3) above. Components $s_{hi}$ corresponding to the selected basis function(s) $A_h$ are regarded as the above-noted image components corresponding to the linear artifacts. In the case of the linear artifacts in this Embodiment 2, as in Embodiment 1 described hereinbefore, the basis function(s) $A_h$ corresponding to the linear artifacts is/are not limited to one, but a plurality of basis functions $A_h$ exist. The technique of obtaining the image components corresponding to the linear artifacts (i.e. components $s_{hi}$ corresponding to the selected basis functions $A_h$) is the same as in foregoing Embodiment 1, and its description is omitted.

With the image components $s_{hi}$ corresponding to the linear artifacts obtained in this way, element images $s_{hi}*A_h$ consisting of basis functions $A_h$ corresponding to the linear artifacts and components $s_{hi}$ corresponding thereto act as image components corresponding to the linear artifacts, i.e. a pixel group including the linear artifacts on the polar coordinates, and a pixel group including the ring artifacts on the rectangular coordinates. And element images $s_{ji}*A_j$ consisting of the remaining basis functions $A_j$ not selected and components $s_{ji}$ corresponding thereto act as image components not corresponding to the linear artifacts, i.e. a pixel group not including the linear artifacts on the polar coordinates, and a pixel group not including the ring artifacts on the rectangular coordinates. Therefore, through the steps in steps T1, S1, S2 and T2, a division is made into the pixel group including the linear artifacts and the pixel group not including the linear artifacts (on the rectangular coordinates). The dividing unit 8b noted above (see FIG. 1) executes the steps in steps T1, S1, S2 and T2.

(Step S4) Replace Components with "0" (Correction Process)

The image components $s_{hi}$ corresponding to the linear artifacts obtained in step T3 are replaced with "0", thereby eliminating the image components $s_{hi}$ corresponding to the linear artifacts. This step S4 is the same as in Embodiment 1 except that the images having the image components replaced with "0" are sectional images F (x, y) in Embodiment 1 while they are images F (r, θ) in this Embodiment 2, and its description is omitted. The pixel group processing unit 8c noted above (see FIG. 1) carries out the correction process in this step S4.

(Step S5) Arrange Element Images

This step S5 is the same as in Embodiment 1 except that the element images are element images $F_i$ (x, y) in Embodiment 1 while they are element images $F_i$ (r, θ) in this Embodiment 2. That is, element images $F_i$ (r, θ) having undergone the correction process in step S4, and element images $F_i$ (r, θ) consisting of the remaining basis functions $A_j$ not selected and components $s_{ji}$ corresponding thereto, are arranged by i=1 to Δ, thereby obtaining images F (r, θ) without the linear artifacts.

(Step T3) Inverse Transform to Rectangular Coordinate System

The images F (r, θ) from which the linear artifacts have been removed in step S5 are inverse transformed to sectional images F (x, y) on the rectangular coordinates of rectangular coordinate system x, y. The sectional images F (x, y) without ring artifacts are obtained by carrying out the inverse transform in this way.

According to steps T1, S1, S2, T2, S4, S5 and T3 in this Embodiment 2, as in foregoing Embodiment 1, the predetermined process relating to correction is performed only with respect to the pixel group including the ring artifacts (actual subjects for correction in this Embodiment 2 being image components $s_{hi}$ corresponding to the linear artifacts transformed to the polar coordinates), and the predetermined process relating to correction is not performed with respect to the pixel group not including the ring artifacts. Proper, normal sectional images formed of the pixel group not including the ring artifacts have hardly any side effects due to a filter such as a reduction in image resolution, and the artifacts (ring artifacts here) can be removed stably.

In this Embodiment 2, sectional images F (x, y) are transformed to images F (r, θ) on the polar coordinates of polar coordinate system r, θ to transform the ring artifacts on sectional images F (x, y) to the linear artifacts on the images F (r, θ). These images F (r, θ) are divided by r, θ into groups, Δ in number, thereby to obtain images $F_i$ (r, θ) (where i=1 to Δ) formed of N pixels. By applying the independent component analysis, each element image $F_i$ (r, θ) is developed with basis functions $A_j$ consisting of N pixels (where j=1 to N). Basis function(s) $A_h$ (where $1 \leq h \leq N$; the number of applicable h being one or more) corresponding to the ring artifacts is/are selected from among the basis functions $A_j$ developed by equation (3) above. Components $s_{hi}$ corresponding to the selected basis function(s) $A_h$ are regarded as image components corresponding to the linear artifacts. A correction process is carried out on each of the element images $F_i$ (r, θ), which replaces the components $s_{hi}$ with "0", thereby eliminating the image components $s_{hi}$ corresponding to the linear artifacts. Images F (r, θ) having the element images $F_i$ (r, θ) arranged by i=1 to Δ are inverse transformed to sectional images F (x, y) on the rectangular coordinates of rectangular coordinate system x, y, thereby obtaining sectional images F (x, y) without the ring artifacts.

In the case of the rectangular coordinate system as in foregoing Embodiment 1, generally, when the size of basis functions $A_j$, i.e. the value of N, is small, since a straight line is a pattern of two directions (x, y), it is easy to detect as a characteristic, and a ring artifact tends to be difficult to detect as a characteristic. In the case of the polar coordinate system as in this Embodiment 2, even if the value of N is small, linear artifacts are easy to detect as a characteristic. The straight lines in this Embodiment 2 have the advantage of being easier to detect than the rings in Embodiment 1.

Embodiment 3

Figure 9:
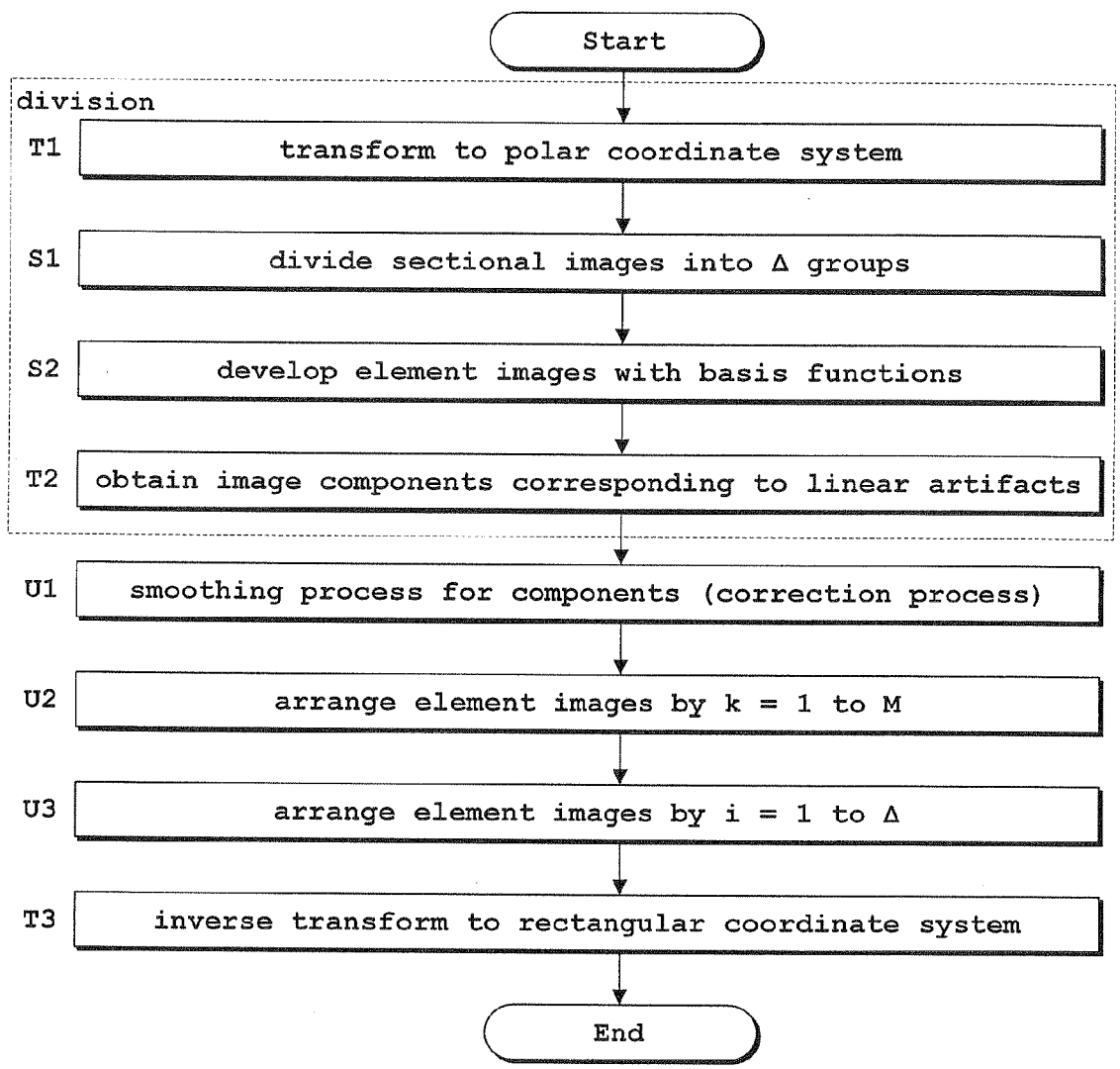
FIG. 9 is a flow chart showing a flow of a series of tomographic steps according to Embodiment 3.
Figure 10:
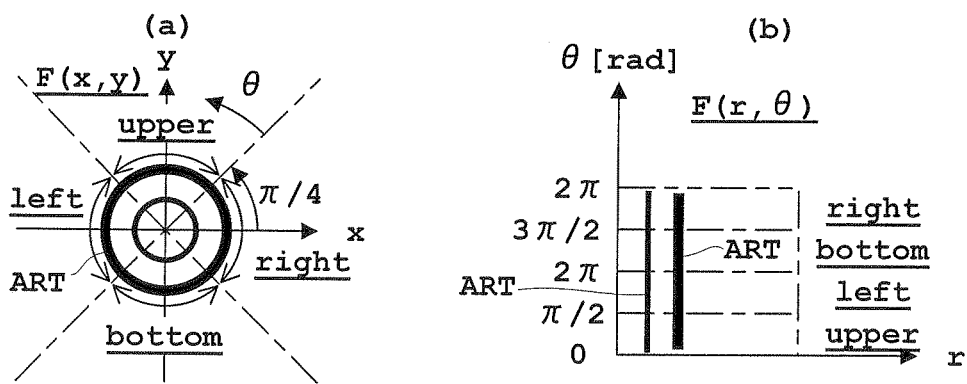
FIGS. 10(a) and (b) are schematic views showing a relationship of each sectional image and artifacts when an area is divided into four parts, and transform is made from a rectangular coordinate system to a polar coordinate system.
Figure 11:
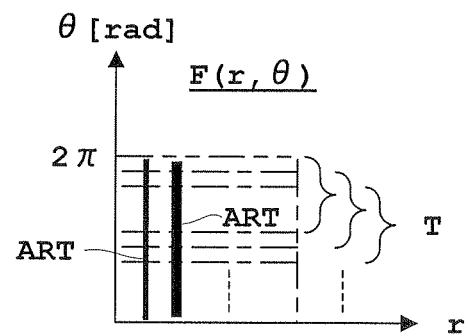
FIG. 11 is a schematic view of the polar coordinate system when the divided areas overlap one another.

Next, Embodiment 3 of this invention will be described with reference to the drawings. FIG. 9 is a flow chart showing a flow of a series of tomographic steps according to Embodiment 3. FIG. 10 is a schematic view showing a relationship of each sectional image and artifacts when the area is divided into four parts, and transform is made from a rectangular coordinate system to a polar coordinate system. FIG. 11 is a schematic view of the polar coordinate system when the divided areas overlap one another. The X-ray CT apparatus according to this Embodiment 3 has the same construction as in foregoing Embodiments 1 and 2, and therefore its description will be omitted. In the flow chart of FIG. 9 according to Embodiment 3, the steps common to foregoing Embodiments 1 and 2 are affixed with the same signs, their description will be omitted, and only differences will be described.

(Step T1) Transform to Polar Coordinate System

This step T1 is the same as in Embodiment 2, and its description is omitted. When a division is made into M (four in FIG. 10) areas by θ as described hereinafter, sectional image F (x, y) is transformed to image F (r, θ) on polar coordinates of polar coordinate system r, θ, ring artifacts ART on sectional image F (x, y) shown in FIG. 10(a) are transformed to linear artifacts ART on image F (r, θ) shown in FIG. 10(b).

When angle θ is set with reference an axis at 45° (π/4 [rad]) between x-axis and y-axis as shown in FIG. 10(a), the area denoted "upper" in FIG. 10(a) becomes an area 0–π/2 [rad] in the polar coordinate system, the area denoted "left" in FIG. 10(a) becomes an area π/2–π [rad] in the polar coordinate system, the area denoted "bottom" in FIG. 10(a) becomes an area π–3π/2 [rad] in the polar coordinate system, and the area denoted "right" in FIG. 10(a) becomes an area 3π/2–2π [rad] in the polar coordinate system.

(Step S1) Divide Sectional Images into Δ Groups

This step S1 is the same as in Embodiment 2, and its description is omitted.

(Step S2) Develop Element Images with Basis Functions

This step S2 is the same as in Embodiment 2, and its description is omitted. Development is made with base functions $A_j$ by equation (3) described in Embodiment 2.

(Step T2) Obtain Image Components Corresponding to Linear Artifacts

Basis function(s) $A_h$ (where $1 \leq h \leq N$; the number of applicable h being one or more) corresponding to linear artifacts is/are selected from among the basis functions $A_j$ developed by equation (3) above. In foregoing Embodiment 2, components $s_{hi}$ corresponding to the selected basis function(s) $A_h$ are regarded as the above-noted image components corresponding to the linear artifacts. In this Embodiment 3, element images $s_{hi}*A_h$ consisting of the selected basis function(s) $A_h$ and components $s_{hi}$ corresponding thereto are regarded as the image components corresponding to the linear artifacts.

That is, the components $s_{hi}$ corresponding to the selected basis functions $A_h$ are not made into "0" as done in foregoing Embodiments 1 and 2, but these components are left intact. Conversely, components $s_{ji}$ corresponding to unselected basis functions $A_j$ are made into "0". Thus, element images $F_h$ (r, θ) consisting of $s_{hi}*A_h$ are obtained by arranging, by i=1 to Δ, element images $s_{hi}*A_h$ consisting of the basis function(s) $A_h$ and the components $s_{hi}$ corresponding thereto, with components $s_{hi}$ corresponding to the selected basis function(s) left intact, and element images $s_{ji}*A_j$ consisting of basis function $A_j$ and components $s_{ji}$ corresponding thereto, with the components $s_{ji}$ corresponding to the unselected basis functions $A_j$ replaced with "0". These element images $F_i$ (r, θ) consisting of $s_{hi}*A_h$ are also a pixel group including the linear artifacts, and are regarded as images formed of linear artifact components.

On the other hand, as in foregoing Embodiments 1 and 2, the components $s_{hi}$ corresponding to the selected basis functions $A_h$ are made into "0" and, conversely, components $s_{ji}$ corresponding to unselected basis functions $A_j$ are not made into "0" but these components are left intact.

Element images $F_j$ (r, θ) consisting of remaining $s_{ji}*A_j$ are obtained by arranging, by i=1 to Δ, element images $s_{hi}*A_h$ consisting of the basis function(s) $A_h$ and the components $s_{hi}$ corresponding thereto, with components $s_{hi}$ corresponding to the selected basis function(s) replaced with "0", and element images $s_{ji}*A_j$ consisting of basis function $A_j$ and components $s_{ji}$ corresponding thereto, with the components $s_{ji}$ corresponding to the unselected basis functions $A_j$ left intact. These element images $F_j$ (r, θ) consisting of $s_{ji}*A_j$ are also a pixel group not including the linear artifacts, and are regarded as images formed of components without linear artifact components.

By executing the steps in these steps T1, S1, S2 and T2, a division is made into the pixel group including the ring artifacts and the pixel group not including the ring artifacts (on the rectangular coordinates). The dividing unit 8b noted above (see FIG. 1) executes the steps in steps T1, S2 and T2.

(Step U1) Smoothing Filter Process for Components (Correction Process)

A smoothing filter is applied to element images $s_{hi}*A_h$ consisting of basis function(s) $A_h$ selected in step T2 and components $s_{hi}$ corresponding thereto, i.e. the image components corresponding to the linear artifacts. That is, a correction process relating to the above smoothing is carried out for element images $F_h$ (r, θ) consisting of $s_{hi}*A_h$.

Specifically, the above element images $F_h$ (r, θ) consisting of element images $s_{hi}*A_h$ are divided by θ into images $F_{hk}$ (r, θ) (where k=1 to M) of M areas (where M is a natural number including 1). Where M=4, the division is made into four areas as noted above. Thus, the division as shown in FIG. 10(a), for example, will result in a division in the polar coordinate system as shown in FIG. 10(b). The division is made without being limited to M. Any number of divisions can be selected by arbitrarily designating 1, 2, 3, . . . as long as it is a natural number. As shown in FIG. 11, the divided areas (see sign "T") in the polar coordinate system may overlap one another. Since M is a natural number including 1, the case where element images $F_h$ (r, θ) are not divided at the time of M=1 is also included.

A profile function $P_k(r)$ is obtained by integrating each divided image $F_{hk}$ (r, θ) with θ. Uniform profile function $P_k(r)$ integrated with θ on polar coordinates of the polar coordinate system r, θ is expressed by the following equation (4):

[Math 4]

$$P_k(r) = \sum_\theta F_{hk}(r, \theta) \tag{4}$$

Since image $F_{hk}$ (r, θ) seen from θ is a discontinuous function, integration is made by addition in equation (4) above. Image $F_{hk}$ (r, θ) may be interpolated, or an approximate function may be obtained, to be continuous as seen from θ, and one-dimensional profile function $P_k(r)$ integrated with θ may be obtained by integrating the interpolated continuous image $F_{hk}$ (r, θ) or continuous approximation function as in the following equation (5):

[Math 5]

$$P_k(r) = \int_\theta F_{hk}(r, \theta) d\theta \tag{5}$$

$P_k(r)'$ is obtained by applying a smoothing filter about r to the one-dimensional profile function $P_k(r)$ derived from equation (4) above or equation (5) above. This smoothing filter may use an additive average (arithmetical average) of $P_k(r)$ or a geometric mean of $P_k(r)$. Any usual smoothing filter may be used (e.g. a gauss type filter, uniform weight smoothing filter, median filter or the like), and there is no limitation in this respect. And a correction is made by substituting image $F_{hk}$ (r, θ) into the right-hand side of the following equation (6) to find a solution to the left-hand side.

[Math 6]

$$F_{hk}(r, \theta) = F_{hk}(r, \theta) * P_k(r)'/P_k(r) \tag{6}$$

(Step U2) Arrange Element Images by K=1 to M

Element images $F_h$ (r, θ) are corrected by arranging, by k=1 to M, the images $F_{hk}$ (r, θ) corrected by equation (6) above. Since M is a natural number including 1 as noted above, the case is also included where element images $F_h$ (r, θ) are corrected by substituting the element images $F_h$ (r, θ), without being divided, into the right-hand side of equation (6) above and finding a solution to the left-hand side. Equation (6) above corresponds to equation (C) in this invention.

Generally, when the value of profile function $P_k(r)$ can be extremely smaller than the value of $P_k(r)'$ resulting from the smoothing, the division as in equation (6) above could increase the influence of noise. Thus, a subtraction as in the following equation (7) is more advantageous. That is, a correction is made by substituting images $F_{hk}$ (r, θ) into the right-hand side of the following equation (7) and finding a solution to the left-hand side.

[Math 7]

$$F_{hk}(r,\theta)=F_{hk}(r,\theta)-(P_k(r)-P_k(r)') \qquad (7)$$

Element images $F_h$ (r, θ) are corrected by arranging, by k=1 to M, the images $F_{hk}$ (r, θ) corrected by equation (7) above. With equation (7) above also, the case is also included where element images $F_h$ (r, θ) are corrected by substituting the element images $F_h$ (r, θ), without being divided, into the right-hand side of equation (7) above and finding a solution to the left-hand side. Equation (7) above corresponds to equation (D) in this invention.

(Step U3) Arrange Element Images by i=1 to Δ

Element images $F_h$ (r, θ) corrected by equation (6) above or equation (7) above, and element images $F_i$ (r, θ) consisting of the remaining basis functions $A_j$ not selected and components $s_{ji}$ corresponding thereto, are arranged by i=1 to Δ, thereby obtaining images F (r, θ) without the linear artifacts.

(Step T3) Inverse Transform to Rectangular Coordinate System

This step T3 is the same as in Embodiment 2. That is, the images F (r, θ) from which the linear artifacts have been removed in step U3 are inverse transformed to sectional images F (x, y) on the rectangular coordinates of rectangular coordinate system x, y. The sectional images F (x, y) without ring artifacts are obtained by carrying out the inverse transform in this way.

According to steps T1, S1, S2, T2, U1-U3 and T3 in this Embodiment 3, as in foregoing Embodiments 1 and 2, the predetermined process relating to correction is performed only with respect to the pixel group including the ring artifacts (actual subjects for correction in this Embodiment 3, as in Embodiment 2, being image components $s_{hi}$ corresponding to the linear artifacts transformed to the polar coordinates), and the predetermined process relating to correction is not performed with respect to the pixel group not including the ring artifacts. Proper, normal sectional images formed of the pixel group not including the ring artifacts have hardly any side effects due to a filter such as a reduction in image resolution, and the artifacts (ring artifacts here) can be removed stably.

In this Embodiment 3, as distinct from foregoing Embodiments 1 and 2, a predetermined process relating to correction is carried out only with respect to the pixel group including the ring artifacts by applying the smoothing filter to the pixel group including the ring artifacts. Compared with the technique as in foregoing Embodiments 1 and 2 which eliminates the image components corresponding to the ring artifacts, side effects due to the filter, such as a reduction in image resolution, on proper, normal sectional images can be further inhibited.

Specifically, in the case of foregoing Embodiments 1 and 2, the number of pixels (i.e. N) forming the basis functions $A_j$ is also the number of basis functions $A_j$ per se. When using basis functions $A_j$ small in size (i.e. the value of N being small) (N=16, for example), there is a possibility that the feature quantity of the images cannot be divided finely enough. As a result, the ring artifacts in the rectangular coordinate system, and basis functions $A_h$ corresponding to the linear artifacts in the polar coordinate system, include certain of components of the proper CT images (components except the artifact components). When, in such a situation, the image components corresponding to the ring artifacts are eliminated by being replaced with "0" according to foregoing Embodiments 1 and 2, the components of the proper, normal sectional images (CT images here) will also be eliminated. This results in blurs or artifacts occurring on the images after the correction. On the other hand, when N is set, for example, to 256 or larger value, an amount of calculation becomes huge although the image quality of the images after the correction improves gradually, and thus becoming difficult to use it in practice. Since the smoothing filter is used in this embodiment 3, such problem will not arise.

In this Embodiment 3, when the smoothing filter is applied to the pixel group including the ring artifacts, the independent component analysis is used as feature quantity analysis as in Embodiments 1 and 2, which may be summarized as follows. That is, using the independent component analysis, a separation is made independently into image components corresponding to the ring artifacts and image components not corresponding to the ring artifacts, thereby dividing into an image group including the ring artifacts and an image group not including the ring artifacts. Then, the smoothing filter noted above is applied to the image components corresponding to the ring artifacts (since, in fact, they are smoothed after being transformed into the polar coordinate system, the smoothing filter is applied to the image components corresponding to the linear artifacts at this time), thereby performing the predetermined process relating to correction only with respect to the pixel group including the ring artifacts. For applying the smoothing filter to the image components corresponding to the ring artifacts (linear artifacts in the polar coordinate system), the transform to the polar coordinate system and the inverse transform to the rectangular coordinate system are carried out as described hereinbefore.

That is, basis function(s) $A_h$ (where 1≤h≤N; the number of applicable h being one or more) corresponding to linear artifacts is/are selected from among the basis functions $A_j$ developed by equation (3) above. Element images $s_{hi}*A_h$ consisting of the selected basis function(s) $A_h$ and components $s_{hi}$ corresponding thereto are regarded as image components corresponding to the linear artifacts. A correction process is carried out on the element images $F_h$ (r, θ) consisting of $s_{hi}*A_h$, which smoothes the image components corresponding to the linear artifacts by applying the smoothing filter to the image components. Images F (r, θ) having the element images $F_h$ (r, θ), and the element images $F_i$ (r, θ) consisting of the remaining basis functions $A_j$ not selected and components $s_{ji}$ corresponding thereto, which are arranged by i=1 to Δ, are inverse transformed to sectional images F (x, y) on the rectangular coordinates of rectangular coordinate system x, y, thereby obtaining sectional images F (x, y) without the ring artifacts.

More particularly, the element images $F_h$ (r, θ) consisting of the element images $s_{hi}*A_h$ are divided by θ into images $F_{hk}$ (r, θ) (where k=1 to M) of M areas (where M is a natural number including 1). A profile function $P_k(r)$ of each image $F_{hk}(r, \theta)$ integrated with θ is obtained. $P_k(r)'$ is obtained by applying the smoothing filter about r to the profile function $P_k(r)$. A correction is made by substituting images $F_{hk}(r, \theta)$, using $P_k(r)'$ obtained, into the right-hand side of equation (6) above or equation (7) above, and finding a solution to the left-hand side. The element images $F_h(r, \theta)$ are corrected by arranging the corrected images $F_{hk}(r, \theta)$ by k=1 to M.

Figure 12:
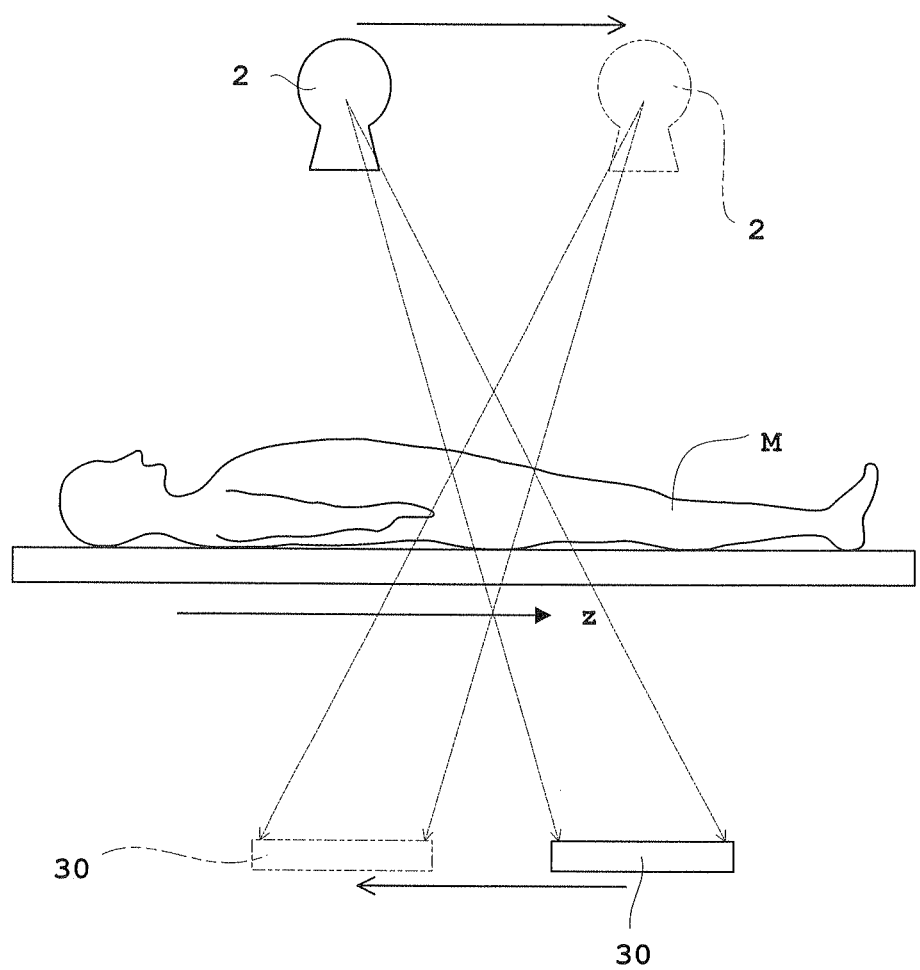
FIG. 12 is a schematic side view of a tomographic apparatus according to a modification.
Figure 13:
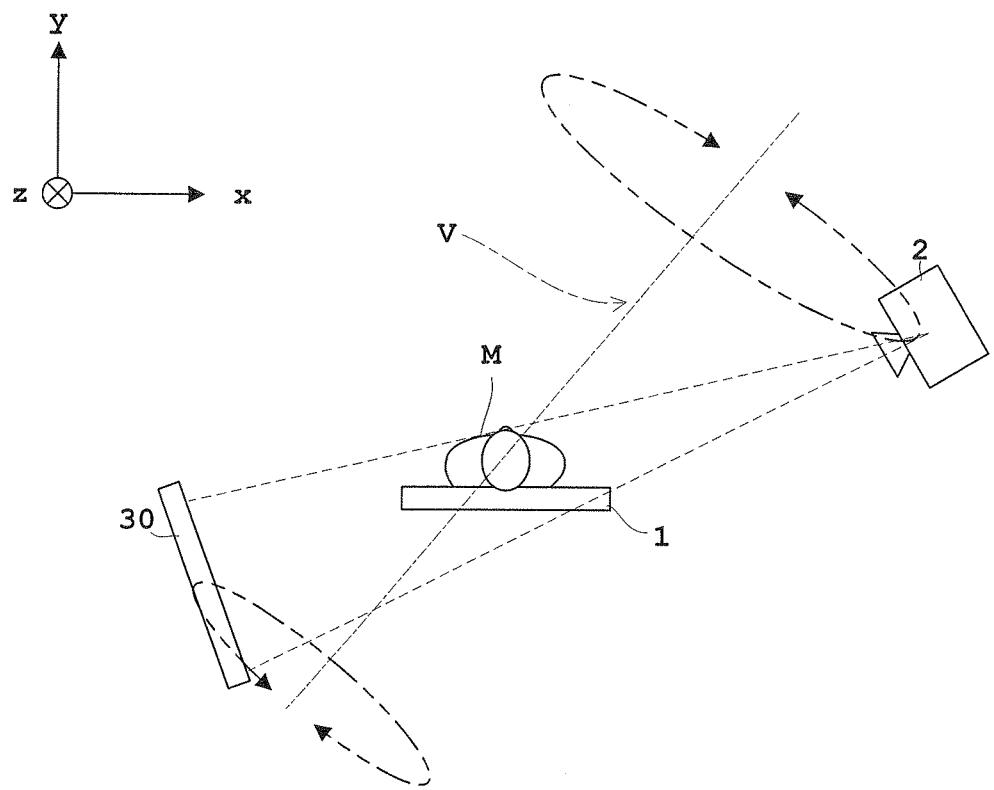
FIG. 13 is a schematic front view of a tomographic apparatus according to a modification.
Figure 14:
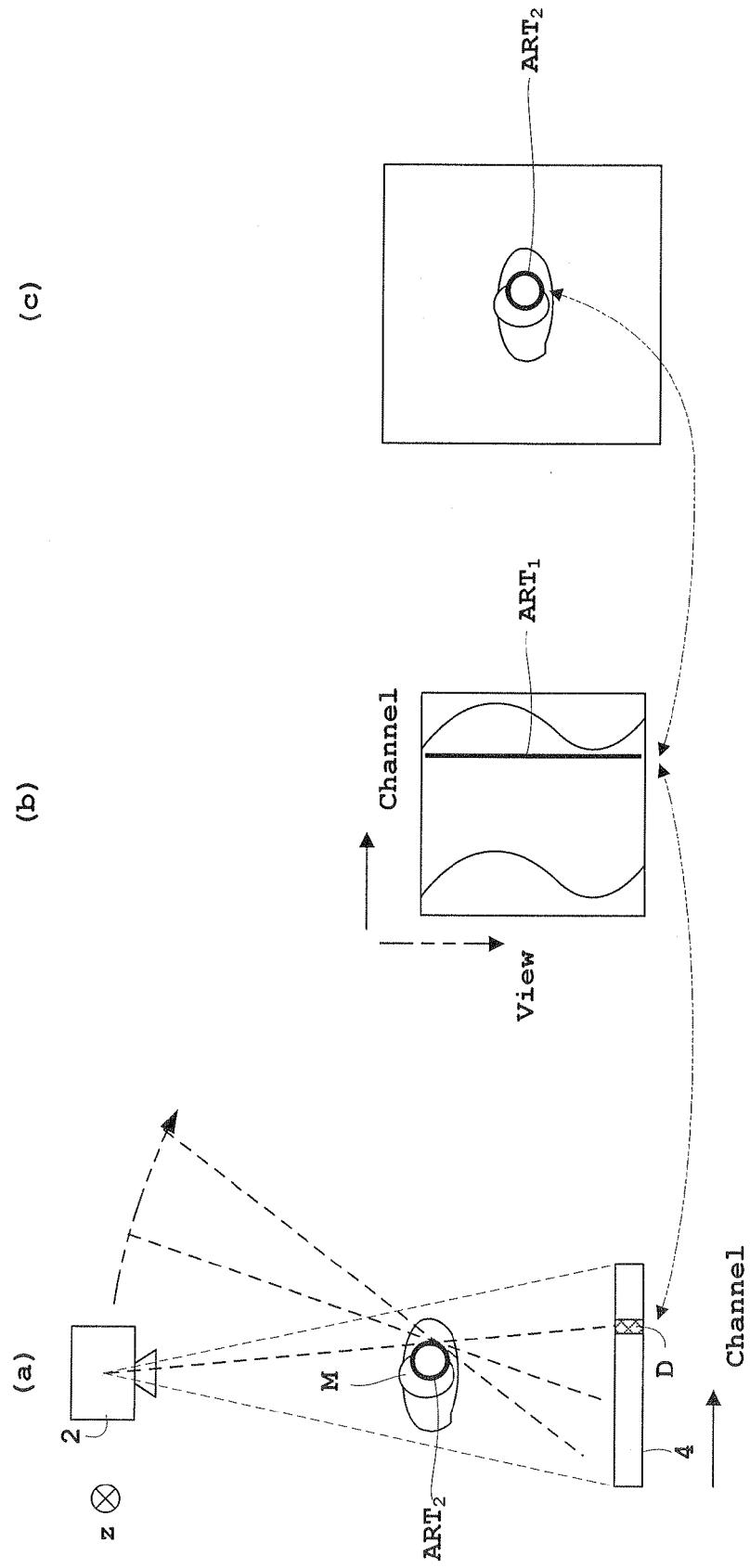
FIGS. 14(a)-(c) are schematic views for use in description of ring artifact generation on a CT image.

This invention is not limited to the foregoing embodiments, but may be modified as follows:

(1) In each of the foregoing embodiments, the X-ray CT apparatus has been described as an example of tomographic apparatus, but the tomographic apparatus is not limited to the X-ray CT apparatus. The invention may be applied to an apparatus as shown in FIG. 12, for example, which performs tomography with an X-ray tube 2 and a flat panel X-ray detector (FPD) 30 moving parallel to each other in opposite directions along the body axis z of a patient M, and to an apparatus as shown in FIG. 13, which performs tomography with an X-ray tube 2 and an FPD 30 making precession movement about an axis V extending perpendicular to the body axis z of a patient M. The axis V may be parallel to the x-axis or y-axis in the drawing, and is not limited as long as it is perpendicular to the body axis. In these cases, the processes in each of the foregoing embodiments are carried out on sectional images obtained by tomography thereof, instead of the CT images described hereinbefore.

(2) Each of the foregoing embodiments has been described taking X-rays for example. The detecting device in this invention may detect radiation other than X-rays (γ-rays in the case of a PET apparatus), such as in a nuclear medical diagnostic apparatus, i.e. an ECT (Emission Computed Tomography) apparatus, represented by a PET (Positron Emission Tomography) apparatus or a SPECT (Single Photon Emission CT) apparatus, and the processes in each of the foregoing embodiments may be carried out on sectional images of a patient relating to the radiation obtained by the detecting device.

(3) Each of the foregoing embodiments has been described taking radiation, typically X-rays, for example. The detecting device in this invention may detect light other than radiation, and the processes in each of the foregoing embodiments may be carried out on sectional images of a patient relating to the light obtained by the detecting device.

(4) Each of the foregoing embodiments has been described taking, for example, the case of providing the emitting device in this invention (X-ray tube in each embodiment). It is not absolutely necessary to provide the emitting device. The invention may be applied to an apparatus, such as the nuclear medical diagnostic apparatus noted above, in which a radioactive substance is introduced into the body of a patient, and the detecting device in this invention detects radiation (e.g. α-rays, β-rays or γ-rays) generated from the patient, thereby obtaining sectional images. The invention may be applied also to a nuclear medical diagnostic apparatus which carried out absorption correction, with an emitting device represented by an external radiation source for emitting radiation of the same type as the radioactive substance. In this case, the processes in each of the foregoing embodiments are carried out on sectional images after the absorption correction.

(5) Each of the foregoing embodiments has been described taking the X-ray tube as an example of the emitting device in this invention. The emitting device may be constructed according to the radiation or light other than X-rays as in modifications (2)-(4) described above. In the case of light, for example, the emitting device may be an LED (light-emitting diode), or a YAG laser for emitting a laser beam.

(6) Each of the foregoing embodiments has been described taking, as an example of the detecting device in this invention, the X-ray detecting array having an arrangement of X-ray detecting elements constructed as cells of a channel as a unit. The detecting device may consist of an X-ray detecting element alone. The detecting device may consist of an image intensifier or X-ray film, for example. Radiation or light other than X-rays may be detected as in modifications (2)-(4) described above. In the case of light, for example, the detecting device may be a photodiode or the like.

(7) Each of the foregoing embodiments has been described taking CT images as an example of sectional images. These may be sectional images other than CT images as in modifications (1)-(4) described above.

(8) In each of the foregoing embodiments, the CT images are images obtained by the emitting device in this invention (X-ray tube in each embodiment) and the detecting device in this invention (X-ray detecting array in each embodiment) revolving about the body axis of a patient. The CT images may be obtained by rotating the patient per se about the body axis. The CT images may be obtained by rotating the patient about the body axis, and at the same time revolving the emitting device in this invention and the detecting device in this invention about the body axis. Therefore, the revolution is not limited to a specific mode as long as the emitting device and detecting device revolve about and relative to the body axis of the patient.

(9) Each of the foregoing embodiments has been described taking, for example, the tomographic apparatus represented by the X-ray CT apparatus. The invention may be applied to an independent image processing apparatus (image processor in each embodiment) without the emitting device in this invention (X-ray tube in each embodiment) and the detecting device in this invention (X-ray detecting array in each embodiment). Therefore, sectional images obtained from a tomographic apparatus acting as an external apparatus may be transferred to the image processing apparatus, and the processes in each of the foregoing embodiments may be carried out on the sectional images in this image processing apparatus.

(10) In each of the foregoing embodiments, the independent component analysis (ICA) has been described as an example of feature quantity analysis. Any feature quantity analysis practiced usually, such as wavelet conversion, for example, may be used instead of being limited to the independent component analysis.

(11) Each of the foregoing embodiments is premised on the technical idea of carrying out a correction process to remove artifacts, by performing a feature quantity analysis of the artifacts to make a division into a pixel group including the artifacts and a pixel group not including the artifacts, and performing a predetermined process relating to correction only with respect to the above pixel group including the artifacts. Instead of being premised on such technical idea, the smoothing filter may be applied to the sectional images by transforming equation (C) above (equation (6) above in Embodiment 3) into the following equation (C)' or transforming equation (D) above (equation (7) above in Embodiment 3) into the following equation (D)'.

That is, sectional images F (x, y) are transformed to images F (r, θ) on polar coordinates of polar coordinate system r, θ, and these images F (r, θ) are divided by θ into images $F_k(r, \theta)$ (where k=1 to M) of M areas (where M is a natural number including 1). A profile function $P_k(r)$ of each image $F_k(r, \theta)$ integrated with θ is obtained. $P_k(r)'$ is obtained by applying the smoothing filter about r to the profile function $P_k(r)$. A correction is made by substituting images $F_k(r, \theta)$ into the right-hand side of the following equation (C)' or the following equation (D)', and finding a solution to the left-hand side.

$$F_k(r,\theta)=F_k(r,\theta)*P_k(r)'/P_k(r) \tag{C}'$$

$$F_k(r,\theta)=F_k(r,\theta)-(P_k(r)-P_k(r)') \tag{D}'$$

The images F (r, θ) are corrected by arranging, by k=1 to M, the images $F_k$ (r, θ) corrected by equation (C)' above or equation (D)' above. These images F (r, θ) are inverse transformed to sectional images F (x, y) on the rectangular coordinates of rectangular coordinate system x, y, thereby obtaining sectional images without the artifacts. In the case of equation (C)' or (D)' it is not absolutely necessary to conduct the feature quantity analysis. Instead of the element images $F_h$ (r, θ) obtained using the feature quantity analysis in each of the foregoing embodiments, the smoothing filter process may be performed on the F (r, θ) transformed to the polar coordinates from the original sectional images F (x, y).

The invention claimed is:

1. An image processing method for processing a sectional image, wherein the sectional image is divided into a pixel group including artifacts and a pixel group without any artifacts by carrying out a feature quantity analysis of the artifacts, and a correction process is carried out to remove the artifacts by performing a predetermined process relating to correction only with respect to the pixel group including the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without any artifacts, wherein the predetermined process relating to correction is performed only with respect to the pixel group including the artifacts by eliminating image components corresponding to the artifacts, wherein, with a sectional plane of the sectional image regarded as an x, y plane, and each pixel of the sectional image regarded as F (x, y), the sectional image F (x, y) is divided by the x, y into groups, Δ in number, thereby to obtain images $F_i$ (x, y) (where i =1 to Δ) formed of N pixels, and by applying the independent component analysis, each element image $F_i$ (x, y) is developed with basis functions $A_j$ consisting of N pixels (where j=1 to N), as in;

$$F_i(x,y)=\Sigma_{j=1}^{N} S_{ji}*A_j \tag{A}$$

and wherein basis function(s) $A_h$, (where 1≦h≦N; the number of applicable h being one or more) corresponding to the artifacts is/are selected from among the basis functions $A_j$ developed by equation (A) above, components $s_{hi}$ corresponding to the selected basis function(s) $A_h$ being regarded as image components corresponding to the artifacts, and the correction process is carried out on each of the element images $F_i$ (x, y), which replaces the components $s_{hi}$ with "0", thereby eliminating the image components corresponding to the artifacts, and the element images $F_i$ (x, y) are arranged by i=1 to Δ, thereby obtaining a sectional image without the artifacts.

2. An image processing method for processing a sectional image, wherein the sectional image is divided into a pixel group including artifacts and a pixel group without any artifacts by carrying out a feature quantity analysis of the artifacts, and a correction process is carried out to remove the artifacts by performing a predetermined process relating to correction only with respect to the pixel group including, the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without any artifacts, wherein the predetermined process relating to correction is performed only with respect to the pixel group including the artifacts by eliminating image components corresponding to the artifacts, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the r, θ into groups, Δ in number, thereby to obtain images $F_i$ (r, θ) (where i=1 to Δ) formed of N pixels, and by applying the independent component analysis, each element image $F_i$ (r, θ) is developed with basis functions $A_j$ consisting of N pixels (where j=1 to N), as in;

$$F_i(r,\theta)=\Sigma_{j=1}^{N} S_{ji}*A_j \tag{B}$$

and wherein basis function(s) $A_h$, (where 1≦h≦N; the number of applicable h being one or more) corresponding to the artifacts is/are selected from among the basis functions $A_j$ developed by equation (B) above, components $s_{hi}$ corresponding to the selected basis function(s) $A_h$ being regarded as image components corresponding to the artifacts, and the correction process is carried out on each of the element images $F_i$ (r, θ), which replaces the components $s_{hi}$ with "0", thereby eliminating the image components corresponding to the artifacts, and an image F (r, θ) having the element images $F_i$, (r, θ) arranged by i=1 to Δ is inverse transformed to a sectional image F (x, y) on rectangular coordinates of rectangular coordinate system x, y, thereby obtaining a sectional image without the artifacts.

3. An image processing method for processing a sectional image, wherein the sectional image is divided into a pixel group including artifacts and a pixel group without any artifacts by carrying out a feature quantity analysis of the artifacts and a correction process is carried out to remove the artifacts by performing a predetermined process relating to correction only with respect to the pixel group including the artifacts, and wherein the feature quantity analysis is an independent component analysis, and using the independent component analysis, a separation is made independently into image components corresponding to the artifacts and image components not corresponding to the artifacts, thereby dividing into the pixel group including the artifacts and the pixel group without any artifacts, wherein the predetermined process relating to correction is performed only with respect to the pixel group including the artifacts by applying a smoothing filter to the pixel group including the artifacts, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the r, θ into groups, Δ in number, thereby to obtain images $F_i$ (r, θ) (where i=1 to Δ) formed of N pixels, and by applying the independent component analysis, each element image $F_i$ (r, θ) is developed with basis functions $A_j$ consisting of N pixels (where j=1 to N), as in;

$$F_i(r,\theta)=\Sigma_{j=1}^{N}S_{ji}*A_j \quad (B)$$

and wherein basis function(s) $A_h$ (where 1≤h≤N; the number of applicable h being one or more) corresponding to the artifacts is/are selected from among the basis functions $A_j$ developed by equation (B) above, element images $s_{hi}*A_h$ consisting of the selected basis function(s) $A_h$ and components $s_{hi}$ corresponding thereto being regarded as image components corresponding to the artifacts, and the correction process is carried out on the element images $F_h$ (r, θ) consisting of $s_{hi}*A_h$, which smoothes the image components corresponding to the artifacts by applying the smoothing filter to the image components, and an image F (r, θ) having the element images $F_h$ (r, θ), and the element images $F_i$ (r, θ) consisting of the remaining basis functions $A_j$ not selected and components $s_{ji}$ corresponding thereto, which are arranged by i=1 to Δ, is inverse transformed to sectional image F (x, y) on the rectangular coordinates of rectangular coordinate system x, y, thereby obtaining a sectional image F (x, y) without the artifacts.

4. The image processing method according to claim 3, wherein the element images $F_h$ (r, θ) consisting of the element images $s_{hi}*A_h$ are divided by the θ into images $F_{hk}$ (r, θ) (where k =1 to M) of M areas (where M is a natural number including 1), a profile function $P_k(r)$ of each of the images $F_{hk}$ (r, θ) integrated with θ is obtained, $P_k(r)'$ is obtained by applying the smoothing filter about the r to the profile function $P_k(r)$, a correction is made by substituting images $F_{hk}$ (r, θ) into the right-hand side of the following equation (C):

$$F_{hk}(r,\theta)=F_{hk}(r,\theta)*P_k(r)'/P_k(r) \quad (C)$$

and finding a solution to the left-hand side, and the element images $F_h$ (r, θ) are corrected by arranging the corrected images $F_{hk}$ (r, θ) by k=1 to M.

5. The image processing method according to claim 3, wherein the element images $F_h$ (r, θ) consisting of the element images $s_{hi}*A_h$ are divided by the θ into images $F_{hk}$ (r, θ) (where k =1 to M) of M areas (where M is a natural number including 1), a profile function $P_k(r)$ of each of the images $F_{hk}$ (r, θ) integrated with θ is obtained, $P_k(r)'$ is obtained by applying the smoothing filter about the r to the profile function $P_k(r)$, a correction is made by substituting images $F_{hk}$ (r, θ) into the right-hand side of the following equation (D):

$$F_{hk}(r,\theta)=F_{hk}(r,\theta)-(P_k(r)-P_k(r)') \quad (D)$$

and finding a solution to the left-hand side, and the element images $F_h(r, \theta)$ are corrected by arranging the corrected images $F_{hk}$ (r, θ) by k =1 to M.

6. An image processing method for processing a sectional image, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the θ into images $F_k$ (r, θ) (where k =1 to M) of M areas (where M is a natural number including 1), a profile function $P_k(r)$ of each of the images $F_k$(r, θ) integrated with θ is obtained, $P_k(r)'$ is obtained by applying a smoothing filter about the r to the profile function $P_k(r)$, a correction is made by substituting images $F_k$ (r, θ), using $P_k(r)'$ obtained, into the right-hand side of the following equation (C)':

$$F_k(r,\theta)=F_k(r,\theta)*P_k(r)'/P_k(r) \quad (C)'$$

and finding a solution to the left-hand side, the image F (r, θ) is corrected by arranging the corrected images $F_k$ (r, θ) by k =1 to M, and this image F (r, θ) is inverse transformed to a sectional image F (x, y) on rectangular coordinates of rectangular coordinate system x, y, thereby obtaining a sectional image without the artifacts.

7. The image processing method according to claim 6, wherein the sectional image is an image obtained by an imaging, system revolving about and relative to a body axis of a patient.

8. An image processing method for processing a sectional image, wherein, with a sectional plane of the sectional image regarded as an x, y plane, and each pixel value of the sectional image regarded as F (x, y), the sectional image F (x, y) is transformed to an image F (r, θ) on polar coordinates of polar coordinate system r, θ to transform the artifacts on the sectional image F (x, y) to artifacts on the image F (r, θ), and this image F (r, θ) is divided by the θ into images $F_k$ (r, θ) (where k =1 to M) of M areas (where M is a natural number including 1), a profile function $P_k(r)$ of each of the images $F_k$ (r, θ) integrated with θ is obtained, $P_k(r)'$ is obtained by applying a smoothing filter about the r to the profile function $P_k(r)$, a correction is made by substituting images $F_k$ (r, θ), using $P_k(r)'$ obtained, into the right-hand side of the following equation (D)':

$$F_k(r,\theta)=F_{hk}(r,\theta)-(P_k(r)-P_k(r)') \quad (D)'$$

and finding a solution to the left-hand side, the image F (r, θ) is corrected by arranging the corrected images $F_k$, (r, θ) by k =1 to M, and this image F (r, θ) is inverse transformed to a sectional image F (x, y) on rectangular coordinates of rectangular coordinate system x, y, thereby obtaining a sectional image without the artifacts.

9. The image processing method according to claim 8, wherein the sectional image is an image obtained by an imaging system revolving about and relative to a body axis of a patient.

* * * * *